(12) United States Patent
Heske et al.

(10) Patent No.: US 10,271,827 B2
(45) Date of Patent: *Apr. 30, 2019

(54) DISPOSABLE BIOPSY UNIT

(71) Applicant: C. R. Bard, Inc., Tempe, AZ (US)

(72) Inventors: Norbert Heske, Kottgeisering (DE); Thomas Heske, Grafrath (DE)

(73) Assignee: C. R. Bard, Inc., Franklin Lake, NJ (US)

( * ) Notice: Subject to any disclaimer, the term of this patent is extended or adjusted under 35 U.S.C. 154(b) by 428 days.

This patent is subject to a terminal disclaimer.

(21) Appl. No.: 15/240,427

(22) Filed: Aug. 18, 2016

(65) Prior Publication Data

US 2016/0374650 A1    Dec. 29, 2016

Related U.S. Application Data

(63) Continuation of application No. 14/729,113, filed on Jun. 3, 2015, now Pat. No. 9,421,002, which is a
(Continued)

(30) Foreign Application Priority Data

Mar. 19, 2002   (DE) .................................. 102 12 139
Mar. 19, 2002   (DE) .................................. 102 12 155
(Continued)

(51) Int. Cl.
 *A61B 10/02*    (2006.01)
 *A61B 17/34*    (2006.01)
(Continued)

(52) U.S. Cl.
 CPC ...... *A61B 10/0283* (2013.01); *A61B 10/0233* (2013.01); *A61B 10/0275* (2013.01);
(Continued)

(58) Field of Classification Search
 CPC ... A61B 34/20; A61B 34/10; A61B 17/32053; A61B 2010/0208; A61B 10/0275; A61B 10/0283; A61B 17/32002
(Continued)

(56) References Cited

U.S. PATENT DOCUMENTS

| 737,293 A | 8/1903 | Summerfeldt |
| 1,585,934 A | 5/1926 | Muir |

(Continued)

FOREIGN PATENT DOCUMENTS

| CN | 101011268 A | 8/2007 |
| CN | 101032420 A | 9/2007 |

(Continued)

OTHER PUBLICATIONS

Maxim; Maxim8606; USB/AC Adapter, Li+ Linear Battery Charger with Integrated 50m Omega Battery Switch in TDFN; http://datasheets.maxim-ic.com/en/ds/MAX8606.pdf; Dec. 2008; pp. 1-14; Rev 1.

*Primary Examiner* — May A Abouelela

(57) ABSTRACT

A biopsy device includes a housing containing an electric power source and a tension slide, wherein the tension slide is configured to be moved to a cocked position against the action of a first spring. A releasable locking mechanism is configured to lock the tension slide in the cocked position. A removable element is configured for insertion into the housing. The removable element has a cutting sheath configured to couple the electric power source to the tension slide. The electric power source is configured to rotate the cutting sheath to move the tension slide to the cocked position.

19 Claims, 15 Drawing Sheets

Related U.S. Application Data continuation of application No. 13/340,115, filed on Dec. 29, 2011, now Pat. No. 9,072,502, which is a continuation of application No. 10/500,522, filed as application No. PCT/DE03/00844 on Mar. 17, 2003, now Pat. No. 8,109,885.

(30) Foreign Application Priority Data

| Mar. 19, 2002 | (DE) | ................. | 102 12 156 |
|---|---|---|---|
| Mar. 19, 2002 | (DE) | ................. | 202 04 361 |
| Mar. 19, 2002 | (DE) | ................. | 202 04 362 |
| Mar. 19, 2002 | (DE) | ................. | 202 04 363 |
| Jun. 19, 2002 | (DE) | ................. | 202 09 525 |
| Jun. 19, 2002 | (DE) | ................. | 202 09 530 |
| Aug. 2, 2002 | (DE) | ................. | 202 11 934 |
| Oct. 17, 2002 | (DE) | ................. | 202 15 962 |

(51) Int. Cl.

| A61M 25/06 | (2006.01) |
| A61M 39/10 | (2006.01) |
| G01N 1/08 | (2006.01) |
| A61B 90/00 | (2016.01) |
| A61B 17/00 | (2006.01) |
| A61M 39/12 | (2006.01) |

(52) U.S. Cl.
CPC .......... *A61B 17/3421* (2013.01); *A61B 90/03* (2016.02); *A61M 25/065* (2013.01); *A61M 39/1055* (2013.01); *G01N 1/08* (2013.01); *A61B 2010/0208* (2013.01); *A61B 2017/00477* (2013.01); *A61B 2017/00911* (2013.01); *A61B 2017/00924* (2013.01); *A61B 2090/036* (2016.02); *A61M 39/12* (2013.01)

(58) Field of Classification Search
USPC ................... 600/562–568; 606/170
See application file for complete search history.

(56) References Cited

U.S. PATENT DOCUMENTS

| 1,663,761 | A | 3/1928 | Johnson |
|---|---|---|---|
| 2,953,934 | A | 9/1960 | Sundt |
| 3,019,733 | A | 2/1962 | Braid |
| 3,224,434 | A | 12/1965 | Molomut et al. |
| 3,289,669 | A | 12/1966 | Dwyer et al. |
| 3,477,423 | A | 11/1969 | Griffith |
| 3,512,519 | A | 5/1970 | Hall |
| 3,561,429 | A | 2/1971 | Jewett et al. |
| 3,565,074 | A | 2/1971 | Foti |
| 3,606,878 | A | 9/1971 | Kellogg |
| 3,727,602 | A | 4/1973 | Hyden et al. |
| 3,732,858 | A | 5/1973 | Banko |
| 3,785,380 | A | 1/1974 | Brumfield |
| 3,800,783 | A | 4/1974 | Jamshidi |
| 3,844,272 | A | 10/1974 | Banko |
| 3,882,849 | A | 5/1975 | Jamshidi |
| 3,889,682 | A | 6/1975 | Denis et al. |
| 3,916,948 | A | 11/1975 | Benjamin |
| 3,996,935 | A | 12/1976 | Banko |
| 4,275,730 | A | 6/1981 | Hussein |
| 4,282,884 | A | 8/1981 | Boebel |
| 4,306,570 | A | 12/1981 | Matthews |
| 4,354,092 | A | 10/1982 | Manabe et al. |
| 4,393,879 | A | 7/1983 | Milgrom |
| 4,445,509 | A | 5/1984 | Auth |
| 4,490,137 | A | 12/1984 | Moukheibir |
| 4,549,554 | A | 10/1985 | Markham |
| 4,577,629 | A | 3/1986 | Martinez |
| 4,589,414 | A | 5/1986 | Yoshida et al. |
| 4,603,694 | A | 8/1986 | Wheeler |
| 4,605,011 | A | 8/1986 | Naslund |
| 4,616,215 | A | 10/1986 | Maddalena |
| 4,617,430 | A | 10/1986 | Bryant |
| 4,620,539 | A | 11/1986 | Andrews et al. |
| 4,643,197 | A | 2/1987 | Greene et al. |
| 4,645,153 | A | 2/1987 | Granzow et al. |
| 4,678,459 | A | 7/1987 | Onik et al. |
| 4,696,298 | A | 9/1987 | Higgins et al. |
| 4,702,260 | A | 10/1987 | Wang |
| 4,706,687 | A | 11/1987 | Rogers |
| 4,776,346 | A | 10/1988 | Beraha et al. |
| 4,792,327 | A | 12/1988 | Swartz |
| 4,832,044 | A | 5/1989 | Garg |
| 4,844,064 | A | 7/1989 | Thimsen et al. |
| 4,844,087 | A | 7/1989 | Garg |
| 4,850,354 | A | 7/1989 | McGurk-Burleson et al. |
| 4,893,635 | A | 1/1990 | de Groot et al. |
| 4,907,598 | A | 3/1990 | Bauer |
| RE33,258 | E | 7/1990 | Onik et al. |
| 4,940,061 | A | 7/1990 | Terwilliger et al. |
| 4,952,817 | A | 8/1990 | Bolan et al. |
| 4,958,625 | A | 9/1990 | Bates et al. |
| 4,967,762 | A | 11/1990 | DeVries |
| 4,986,278 | A | 1/1991 | Ravid et al. |
| 4,986,279 | A | 1/1991 | O'Neill |
| 4,986,807 | A | 1/1991 | Farr |
| 4,989,614 | A | 2/1991 | Dejter, Jr. et al. |
| 5,025,797 | A | 6/1991 | Baran |
| 5,048,538 | A | 9/1991 | Terwilliger et al. |
| 5,057,822 | A | 10/1991 | Hoffman |
| 5,078,603 | A | 1/1992 | Cohen |
| 5,125,413 | A | 6/1992 | Baran |
| 5,138,245 | A | 8/1992 | Mattinger et al. |
| 5,146,921 | A | 9/1992 | Terwilliger et al. |
| 5,156,160 | A | 10/1992 | Bennett |
| 5,158,528 | A | 10/1992 | Walker et al. |
| 5,172,702 | A | 12/1992 | Leigh et al. |
| 5,176,628 | A | 1/1993 | Charles et al. |
| 5,183,052 | A | 2/1993 | Terwilliger |
| 5,197,484 | A * | 3/1993 | Kornberg ........... A61B 10/0266 600/567 |
| 5,211,627 | A | 5/1993 | William |
| 5,223,012 | A | 6/1993 | Best et al. |
| 5,225,763 | A | 7/1993 | Krohn et al. |
| 5,234,000 | A | 8/1993 | Hakky et al. |
| 5,236,334 | A | 8/1993 | Bennett |
| 5,242,404 | A | 9/1993 | Conley et al. |
| 5,249,583 | A | 10/1993 | Mallaby |
| 5,254,117 | A | 10/1993 | Rigby et al. |
| 5,282,476 | A | 2/1994 | Terwilliger |
| 5,282,477 | A | 2/1994 | Bauer |
| 5,284,156 | A * | 2/1994 | Schramm ........... A61B 10/0275 600/567 |
| 5,290,253 | A | 3/1994 | Kira |
| 5,305,762 | A | 4/1994 | Acorn et al. |
| 5,324,306 | A | 6/1994 | Makower et al. |
| 5,334,183 | A | 8/1994 | Wuchinich |
| 5,335,671 | A | 8/1994 | Clement |
| 5,368,029 | A | 11/1994 | Holcombe et al. |
| 5,368,045 | A | 11/1994 | Clement et al. |
| 5,383,874 | A | 1/1995 | Jackson et al. |
| 5,397,462 | A | 3/1995 | Higashijima et al. |
| 5,400,798 | A | 3/1995 | Baran |
| 5,439,474 | A | 8/1995 | Li |
| 5,458,112 | A | 10/1995 | Weaver |
| 5,469,860 | A | 11/1995 | De Santis |
| 5,471,994 | A | 12/1995 | Guirguis |
| 5,479,486 | A | 12/1995 | Saji |
| 5,485,917 | A | 1/1996 | Early |
| 5,492,130 | A | 2/1996 | Chiou |
| 5,511,556 | A | 4/1996 | DeSantis |
| 5,526,822 | A | 6/1996 | Burbank et al. |
| 5,535,755 | A | 7/1996 | Heske |
| 5,546,957 | A | 8/1996 | Heske |
| 5,554,151 | A | 9/1996 | Hinchliffe |
| 5,560,373 | A | 10/1996 | De Santis |
| 5,564,436 | A | 10/1996 | Hakky et al. |
| 5,569,284 | A | 10/1996 | Young et al. |

(56) References Cited

U.S. PATENT DOCUMENTS

| | | | |
|---|---|---|---|
| 5,570,699 A * | 11/1996 | Kass | A61B 10/0275 600/567 |
| 5,575,293 A | 11/1996 | Miller et al. | |
| 5,591,170 A | 1/1997 | Spievack et al. | |
| 5,601,583 A | 2/1997 | Donahue et al. | |
| 5,601,585 A | 2/1997 | Banik et al. | |
| 5,602,449 A | 2/1997 | Krause et al. | |
| 5,612,738 A | 3/1997 | Kim | |
| 5,617,874 A | 4/1997 | Baran | |
| 5,649,547 A | 7/1997 | Ritchart et al. | |
| 5,655,542 A | 8/1997 | Weilandt | |
| 5,655,657 A | 8/1997 | Roshdy | |
| 5,660,186 A * | 8/1997 | Bachir | A61B 10/0233 600/562 |
| 5,665,101 A | 9/1997 | Becker et al. | |
| 5,669,394 A | 9/1997 | Bergey et al. | |
| 5,699,909 A | 12/1997 | Foster | |
| 5,700,265 A | 12/1997 | Romano | |
| 5,709,697 A | 1/1998 | Ratcliff et al. | |
| 5,720,760 A | 2/1998 | Becker et al. | |
| 5,735,264 A | 4/1998 | Siczek et al. | |
| 5,752,923 A | 5/1998 | Terwilliger | |
| 5,755,714 A | 5/1998 | Murphy-Chutorian | |
| 5,766,135 A | 6/1998 | Terwilliger | |
| 5,769,086 A | 6/1998 | Ritchart et al. | |
| 5,769,795 A | 6/1998 | Terwilliger | |
| 5,775,333 A | 7/1998 | Burbank et al. | |
| 5,779,649 A | 7/1998 | Herbert | |
| 5,788,651 A | 8/1998 | Weilandt | |
| 5,792,167 A | 8/1998 | Kablik et al. | |
| 5,807,282 A | 9/1998 | Fowler | |
| 5,817,033 A | 10/1998 | DeSantis et al. | |
| 5,817,034 A | 10/1998 | Milliman et al. | |
| 5,823,970 A | 10/1998 | Terwilliger | |
| 5,827,305 A | 10/1998 | Gordon | |
| 5,830,219 A | 11/1998 | Bird et al. | |
| D403,405 S | 12/1998 | Terwilliger | |
| 5,857,982 A | 1/1999 | Milliman et al. | |
| 5,871,699 A | 2/1999 | Ruggeri | |
| 5,879,365 A | 3/1999 | Whitfield et al. | |
| 5,908,233 A | 6/1999 | Heskett et al. | |
| 5,913,857 A | 6/1999 | Ritchart et al. | |
| 5,916,198 A | 6/1999 | Dillow | |
| 5,916,229 A | 6/1999 | Evans | |
| 5,928,164 A | 7/1999 | Burbank et al. | |
| 5,944,673 A | 8/1999 | Gregoire et al. | |
| 5,951,490 A | 9/1999 | Fowler | |
| 5,951,575 A | 9/1999 | Bolduc et al. | |
| 5,964,716 A | 10/1999 | Gregoire et al. | |
| 5,971,939 A | 10/1999 | DeSantis et al. | |
| 5,976,164 A | 11/1999 | Bencini et al. | |
| 5,980,469 A | 11/1999 | Burbank et al. | |
| 5,980,545 A | 11/1999 | Pacala et al. | |
| 6,007,495 A | 12/1999 | Matula | |
| 6,007,497 A | 12/1999 | Huitema | |
| 6,007,556 A | 12/1999 | Kablik et al. | |
| 6,017,316 A | 1/2000 | Ritchart et al. | |
| 6,018,227 A | 1/2000 | Kumar et al. | |
| 6,019,733 A | 2/2000 | Farascioni | |
| 6,022,324 A | 2/2000 | Skinner | |
| 6,022,325 A | 2/2000 | Siczek et al. | |
| 6,027,458 A | 2/2000 | Janssens | |
| 6,032,673 A | 3/2000 | Savage et al. | |
| 6,036,657 A | 3/2000 | Milliman et al. | |
| 6,050,955 A | 4/2000 | Bryan et al. | |
| 6,055,870 A | 5/2000 | Jaeger | |
| 6,071,247 A | 6/2000 | Kennedy | |
| 6,077,230 A | 6/2000 | Gregoire et al. | |
| 6,083,176 A | 7/2000 | Terwilliger | |
| 6,083,237 A | 7/2000 | Huitema et al. | |
| 6,086,544 A | 7/2000 | Hibner et al. | |
| 6,106,484 A | 8/2000 | Terwilliger | |
| 6,110,129 A | 8/2000 | Terwilliger | |
| 6,120,462 A | 9/2000 | Hibner et al. | |
| 6,123,957 A | 9/2000 | Jernberg | |
| 6,126,617 A | 10/2000 | Weilandt et al. | |
| 6,142,955 A | 11/2000 | Farascioni et al. | |
| 6,162,187 A | 12/2000 | Buzzard et al. | |
| 6,165,136 A | 12/2000 | Nishtala | |
| 6,193,673 B1 | 2/2001 | Viola et al. | |
| 6,196,978 B1 | 3/2001 | Weilandt et al. | |
| 6,213,957 B1 | 4/2001 | Milliman et al. | |
| 6,220,248 B1 | 4/2001 | Voegele et al. | |
| 6,231,522 B1 | 5/2001 | Voegele et al. | |
| 6,241,687 B1 | 6/2001 | Voegele et al. | |
| 6,267,759 B1 | 7/2001 | Quick | |
| 6,273,861 B1 | 8/2001 | Bates et al. | |
| 6,273,862 B1 | 8/2001 | Privitera et al. | |
| 6,280,398 B1 | 8/2001 | Ritchart et al. | |
| 6,283,925 B1 | 9/2001 | Terwilliger | |
| 6,322,523 B2 | 11/2001 | Weilandt et al. | |
| 6,328,701 B1 | 12/2001 | Terwilliger | |
| 6,331,166 B1 | 12/2001 | Burbank et al. | |
| 6,358,217 B1 | 3/2002 | Bourassa | |
| 6,402,701 B1 | 6/2002 | Kaplan et al. | |
| 6,419,641 B1 | 7/2002 | Mark et al. | |
| 6,428,486 B2 | 8/2002 | Ritchart et al. | |
| 6,428,487 B1 | 8/2002 | Burdorff et al. | |
| 6,432,064 B1 | 8/2002 | Hibner et al. | |
| 6,432,065 B1 | 8/2002 | Burdorff et al. | |
| 6,434,507 B1 | 8/2002 | Clayton et al. | |
| 6,436,054 B1 | 8/2002 | Viola et al. | |
| 6,461,302 B1 | 10/2002 | Thompson | |
| 6,471,659 B2 | 10/2002 | Eggers et al. | |
| 6,482,158 B2 | 11/2002 | Mault | |
| 6,485,436 B1 | 11/2002 | Truckai et al. | |
| 6,488,636 B2 | 12/2002 | Bryan et al. | |
| 6,494,844 B1 | 12/2002 | Van Bladel et al. | |
| 6,527,736 B1 | 3/2003 | Attinger et al. | |
| 6,540,694 B1 | 4/2003 | Van Bladel et al. | |
| 6,540,761 B2 | 4/2003 | Houser | |
| 6,544,194 B1 | 4/2003 | Kortenbach et al. | |
| 6,551,255 B2 | 4/2003 | Van Bladel et al. | |
| 6,554,779 B2 | 4/2003 | Viola et al. | |
| 6,585,664 B2 | 7/2003 | Burdorff et al. | |
| 6,585,694 B1 | 7/2003 | Smith et al. | |
| 6,586,585 B1 | 7/2003 | Bastian | |
| 6,592,530 B1 * | 7/2003 | Farhadi | A61B 10/0275 600/564 |
| 6,626,849 B2 | 9/2003 | Huitema et al. | |
| 6,632,182 B1 | 10/2003 | Treat | |
| 6,638,235 B2 | 10/2003 | Miller et al. | |
| 6,656,133 B2 | 12/2003 | Voegele et al. | |
| 6,659,105 B2 | 12/2003 | Burbank et al. | |
| 6,659,338 B1 | 12/2003 | Dittmann et al. | |
| 6,683,439 B2 | 1/2004 | Takano et al. | |
| 6,689,072 B2 | 2/2004 | Kaplan et al. | |
| 6,695,786 B2 | 2/2004 | Wang et al. | |
| 6,702,832 B2 | 3/2004 | Ross et al. | |
| 6,712,773 B1 | 3/2004 | Viola | |
| 6,712,774 B2 | 3/2004 | Voegele et al. | |
| 6,752,768 B2 | 6/2004 | Burdorff et al. | |
| 6,753,671 B1 | 6/2004 | Harvey | |
| 6,755,802 B2 | 6/2004 | Bell | |
| 6,758,824 B1 * | 7/2004 | Miller | A61B 10/025 600/566 |
| 6,764,495 B2 | 7/2004 | Lee et al. | |
| 6,832,990 B2 | 12/2004 | Kortenbach et al. | |
| 6,849,080 B2 | 2/2005 | Lee et al. | |
| 6,850,159 B1 | 2/2005 | Mudge | |
| 6,860,860 B2 | 3/2005 | Viola | |
| 6,875,183 B2 | 4/2005 | Cervi | |
| 6,887,210 B2 | 5/2005 | Quay | |
| 6,908,440 B2 | 6/2005 | Fisher | |
| D508,458 S | 8/2005 | Solland et al. | |
| 6,926,676 B2 | 8/2005 | Turturro et al. | |
| 6,984,213 B2 | 1/2006 | Horner et al. | |
| 7,004,174 B2 | 2/2006 | Eggers et al. | |
| 7,010,332 B1 | 3/2006 | Irvin et al. | |
| 7,025,732 B2 | 4/2006 | Thompson et al. | |
| D525,583 S | 7/2006 | Vu | |
| 7,108,660 B2 | 9/2006 | Stephens et al. | |
| 7,153,274 B2 | 12/2006 | Stephens et al. | |
| 7,156,814 B1 | 1/2007 | Williamson, IV et al. | |

(56) References Cited

U.S. PATENT DOCUMENTS

| | | |
|---|---|---|
| 7,182,754 B2 | 2/2007 | Brigham et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,252,641 B2 | 8/2007 | Thompson et al. |
| 7,276,032 B2 | 10/2007 | Hibner |
| 7,328,794 B2 | 2/2008 | Lubs et al. |
| 7,347,828 B2 | 3/2008 | Francese et al. |
| 7,347,829 B2 | 3/2008 | Mark et al. |
| 7,374,544 B2 | 5/2008 | Freeman et al. |
| 7,390,306 B2 | 6/2008 | Mark |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,432,813 B2 | 10/2008 | Postma |
| 7,452,367 B2 | 11/2008 | Rassman et al. |
| 7,458,940 B2 | 12/2008 | Miller |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,491,177 B2 | 2/2009 | Hibner |
| 7,494,473 B2 | 2/2009 | Eggers et al. |
| 7,497,833 B2 | 3/2009 | Miller |
| 7,510,534 B2 | 3/2009 | Burdorff et al. |
| 7,513,877 B2 | 4/2009 | Viola |
| 7,517,321 B2 | 4/2009 | McCullough et al. |
| 7,517,322 B2 | 4/2009 | Weikel, Jr. et al. |
| 7,549,978 B2 | 6/2009 | Carlson et al. |
| 7,575,557 B2 | 8/2009 | Morton et al. |
| 7,648,466 B2 | 1/2010 | Stephens et al. |
| 7,670,299 B2 | 3/2010 | Beckman et al. |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,758,515 B2 | 7/2010 | Hibner |
| 7,762,961 B2 | 7/2010 | Heske et al. |
| 7,806,834 B2 | 10/2010 | Beckman et al. |
| 7,828,746 B2 | 11/2010 | Teague |
| 7,828,747 B2 | 11/2010 | Heske et al. |
| 7,841,991 B2 | 11/2010 | Douglas et al. |
| 7,846,109 B2 | 12/2010 | Parihar et al. |
| 7,854,706 B2 | 12/2010 | Hibner |
| 7,862,517 B2 | 1/2011 | Tsonton et al. |
| 7,862,518 B2 | 1/2011 | Parihar |
| 7,871,384 B2 | 1/2011 | Thompson et al. |
| 7,883,476 B2 | 2/2011 | Miller et al. |
| 7,883,494 B2 | 2/2011 | Martin |
| 7,906,076 B2 | 3/2011 | Fischer |
| 7,914,462 B2 | 3/2011 | Hutchins et al. |
| 7,959,580 B2 | 6/2011 | Mccullough et al. |
| 7,974,681 B2 | 7/2011 | Wallace et al. |
| 8,002,713 B2 | 8/2011 | Heske et al. |
| 8,012,102 B2 | 9/2011 | McCullough et al. |
| 8,016,772 B2 | 9/2011 | Heske et al. |
| 8,016,844 B2 | 9/2011 | Privitera et al. |
| 8,052,614 B2 | 11/2011 | Heske et al. |
| 8,052,615 B2 | 11/2011 | Reuber et al. |
| 8,057,402 B2 | 11/2011 | Hibner et al. |
| 8,073,008 B2 | 12/2011 | Mehta et al. |
| 8,075,495 B2 | 12/2011 | Andreyko et al. |
| 8,083,687 B2 | 12/2011 | Parihar |
| 8,118,755 B2 | 2/2012 | Hibner et al. |
| 8,152,738 B2 | 4/2012 | Li et al. |
| 8,157,744 B2 | 4/2012 | Jorgensen et al. |
| 8,162,851 B2 | 4/2012 | Heske et al. |
| 8,172,771 B2 | 5/2012 | Miller et al. |
| 8,172,773 B2 | 5/2012 | Heske et al. |
| 8,187,204 B2 | 5/2012 | Miller et al. |
| 8,190,238 B2 | 5/2012 | Moll et al. |
| 8,206,409 B2 | 6/2012 | Privitera et al. |
| 8,251,916 B2 | 8/2012 | Speeg et al. |
| 8,251,917 B2 | 8/2012 | Almazan |
| 8,262,586 B2 | 9/2012 | Anderson et al. |
| 8,277,393 B2 | 10/2012 | Miller et al. |
| 8,283,890 B2 | 10/2012 | Videbaek |
| 8,287,465 B2 | 10/2012 | Hardin et al. |
| 8,313,444 B2 | 11/2012 | Thompson et al. |
| 8,343,069 B2 | 1/2013 | Uchiyama et al. |
| 8,366,636 B2 | 2/2013 | Videbaek |
| 8,430,824 B2 | 4/2013 | Videbaek et al. |
| 8,430,825 B2 | 4/2013 | Mark |
| 8,485,987 B2 | 7/2013 | Videbaek et al. |
| 8,485,989 B2 | 7/2013 | Videbaek |
| 8,597,205 B2 | 12/2013 | Seiger et al. |
| 8,597,206 B2 | 12/2013 | Videbaek |
| 8,864,680 B2 | 10/2014 | Videbaek et al. |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0000403 A1 | 1/2002 | Tanaka et al. |
| 2002/0016555 A1 | 2/2002 | Ritchart et al. |
| 2002/0029007 A1 | 3/2002 | Bryan et al. |
| 2002/0045840 A1 | 4/2002 | Voegele et al. |
| 2002/0045842 A1 | 4/2002 | Van Bladel et al. |
| 2002/0065474 A1 | 5/2002 | Viola |
| 2002/0067151 A1 | 6/2002 | Tanishita |
| 2002/0068878 A1 | 6/2002 | Jasonni et al. |
| 2002/0082518 A1 | 6/2002 | Weiss et al. |
| 2002/0082519 A1 | 6/2002 | Miller et al. |
| 2002/0107043 A1 | 8/2002 | Adamson et al. |
| 2002/0115942 A1 | 8/2002 | Stanford et al. |
| 2002/0120212 A1 | 8/2002 | Ritchart et al. |
| 2002/0138020 A1* | 9/2002 | Pflueger ............ A61B 10/0266 600/562 |
| 2002/0138021 A1* | 9/2002 | Pflueger ............ A61B 10/0266 600/565 |
| 2002/0143269 A1 | 10/2002 | Neuenfeldt |
| 2002/0151822 A1 | 10/2002 | Burdorff et al. |
| 2002/0156395 A1 | 10/2002 | Stephens et al. |
| 2002/0193705 A1* | 12/2002 | Burbank ............ A61B 10/0233 600/562 |
| 2003/0023188 A1 | 1/2003 | Kritzman et al. |
| 2003/0023239 A1 | 1/2003 | Burbank et al. |
| 2003/0093103 A1 | 5/2003 | Malackowski et al. |
| 2003/0130593 A1 | 7/2003 | Gonzalez |
| 2003/0130677 A1 | 7/2003 | Whitman et al. |
| 2003/0163142 A1 | 8/2003 | Paltieli et al. |
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0034280 A1 | 2/2004 | Privitera et al. |
| 2004/0049128 A1 | 3/2004 | Miller et al. |
| 2004/0054299 A1 | 3/2004 | Burdorff et al. |
| 2004/0082915 A1 | 4/2004 | Kadan |
| 2004/0092980 A1 | 5/2004 | Cesarini et al. |
| 2004/0092992 A1 | 5/2004 | Adams et al. |
| 2004/0162505 A1 | 8/2004 | Kaplan et al. |
| 2004/0167428 A1 | 8/2004 | Quick et al. |
| 2004/0186393 A1 | 9/2004 | Leigh et al. |
| 2004/0210161 A1 | 10/2004 | Burdorff et al. |
| 2004/0215103 A1 | 10/2004 | Mueller, Jr. et al. |
| 2004/0220495 A1 | 11/2004 | Cahir et al. |
| 2004/0230135 A1 | 11/2004 | Merkle |
| 2004/0230188 A1 | 11/2004 | Cioanta et al. |
| 2004/0249278 A1 | 12/2004 | Krause |
| 2004/0249307 A1 | 12/2004 | Thompson et al. |
| 2004/0267157 A1 | 12/2004 | Miller et al. |
| 2005/0004492 A1 | 1/2005 | Burbank et al. |
| 2005/0004559 A1 | 1/2005 | Quick |
| 2005/0010131 A1 | 1/2005 | Burbank et al. |
| 2005/0020909 A1 | 1/2005 | Moctezuma de la Barrera et al. |
| 2005/0027210 A1 | 2/2005 | Miller |
| 2005/0049489 A1 | 3/2005 | Foerster et al. |

(56) References Cited

U.S. PATENT DOCUMENTS

| | | |
|---|---|---|
| 2005/0049521 A1 | 3/2005 | Miller et al. |
| 2005/0054947 A1 | 3/2005 | Goldenberg |
| 2005/0065453 A1 | 3/2005 | Shabaz et al. |
| 2005/0085838 A1 | 4/2005 | Thompson et al. |
| 2005/0088120 A1 | 4/2005 | Avis |
| 2005/0101879 A1 | 5/2005 | Shidham et al. |
| 2005/0113715 A1 | 5/2005 | Schwindt et al. |
| 2005/0113716 A1 | 5/2005 | Mueller, Jr. et al. |
| 2005/0124914 A1 | 6/2005 | Dicarlo et al. |
| 2005/0124915 A1 | 6/2005 | Eggers et al. |
| 2005/0165328 A1 | 7/2005 | Heske et al. |
| 2005/0177117 A1 | 8/2005 | Crocker et al. |
| 2005/0193451 A1 | 9/2005 | Quistgaard et al. |
| 2005/0203439 A1 | 9/2005 | Heske et al. |
| 2005/0209530 A1 | 9/2005 | Pflueger |
| 2005/0215921 A1 | 9/2005 | Hibner et al. |
| 2005/0275378 A1 | 12/2005 | Canino et al. |
| 2005/0277829 A1 | 12/2005 | Tsonton et al. |
| 2005/0277871 A1 | 12/2005 | Sells |
| 2005/0288605 A1 | 12/2005 | Pellegrino et al. |
| 2006/0030784 A1 | 2/2006 | Miller et al. |
| 2006/0074344 A1 | 4/2006 | Hibner |
| 2006/0074345 A1 | 4/2006 | Hibner |
| 2006/0113958 A1 | 6/2006 | Lobert et al. |
| 2006/0116603 A1 | 6/2006 | Shibazaki et al. |
| 2006/0122535 A1 | 6/2006 | Daum |
| 2006/0129063 A1 | 6/2006 | Thompson et al. |
| 2006/0149162 A1 | 7/2006 | Daw et al. |
| 2006/0178666 A1 | 8/2006 | Cosman et al. |
| 2006/0184063 A1 | 8/2006 | Miller |
| 2006/0200042 A1 | 9/2006 | Weikel, Jr. et al. |
| 2006/0241515 A1 | 10/2006 | Jones et al. |
| 2006/0258956 A1 | 11/2006 | Haberstich et al. |
| 2006/0260994 A1 | 11/2006 | Mark et al. |
| 2007/0016101 A1 | 1/2007 | Feldman et al. |
| 2007/0027407 A1 | 2/2007 | Miller |
| 2007/0032741 A1 | 2/2007 | Hibner et al. |
| 2007/0032743 A1 | 2/2007 | Hibner |
| 2007/0055173 A1 | 3/2007 | DeLonzor et al. |
| 2007/0073326 A1 | 3/2007 | Miller et al. |
| 2007/0090788 A1 | 4/2007 | Hansford et al. |
| 2007/0106176 A1 | 5/2007 | Mark et al. |
| 2007/0118048 A1 | 5/2007 | Stephens et al. |
| 2007/0118049 A1 | 5/2007 | Viola |
| 2007/0161925 A1 | 7/2007 | Quick et al. |
| 2007/0167782 A1 | 7/2007 | Callahan et al. |
| 2007/0167828 A1 | 7/2007 | Saadat |
| 2007/0167943 A1 | 7/2007 | Janssen et al. |
| 2007/0179401 A1 | 8/2007 | Hibner |
| 2007/0213590 A1 | 9/2007 | Squicciarini |
| 2007/0213630 A1 | 9/2007 | Beckman et al. |
| 2007/0213632 A1 | 9/2007 | Okazaki et al. |
| 2007/0219572 A1 | 9/2007 | Deck et al. |
| 2007/0236180 A1 | 10/2007 | Rodgers |
| 2007/0239067 A1 | 10/2007 | Hibner et al. |
| 2007/0255173 A1 | 11/2007 | Hibner |
| 2007/0270710 A1 | 11/2007 | Frass et al. |
| 2007/0276288 A1 | 11/2007 | Khaw |
| 2007/0287933 A1 | 12/2007 | Phan et al. |
| 2007/0292858 A1 | 12/2007 | Chen et al. |
| 2007/0293788 A1 | 12/2007 | Entrekin et al. |
| 2007/0293830 A1 | 12/2007 | Martin |
| 2008/0004545 A1 | 1/2008 | Garrison |
| 2008/0007217 A1 | 1/2008 | Riley |
| 2008/0015429 A1 | 1/2008 | Tsonton et al. |
| 2008/0021487 A1 | 1/2008 | Heisler |
| 2008/0021488 A1 | 1/2008 | Berberich |
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0079391 A1 | 4/2008 | Schroeck et al. |
| 2008/0103411 A1 | 5/2008 | Van Bladel et al. |
| 2008/0110261 A1 | 5/2008 | Randall et al. |
| 2008/0125634 A1 | 5/2008 | Ryan et al. |
| 2008/0135443 A1 | 6/2008 | Frojd et al. |
| 2008/0146962 A1 | 6/2008 | Ritchie et al. |
| 2008/0146965 A1 | 6/2008 | Privitera et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bickenbach |
| 2008/0214955 A1 | 9/2008 | Speeg et al. |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0228104 A1 | 9/2008 | Uber et al. |
| 2008/0232604 A1 | 9/2008 | Dufresne et al. |
| 2008/0234715 A1 | 9/2008 | Pesce et al. |
| 2008/0281225 A1 | 11/2008 | Spero et al. |
| 2008/0306406 A1 | 12/2008 | Thompson et al. |
| 2008/0308607 A1 | 12/2008 | Timm et al. |
| 2008/0319341 A1 | 12/2008 | Taylor et al. |
| 2009/0030405 A1 | 1/2009 | Quick et al. |
| 2009/0048532 A1 | 2/2009 | Stephens et al. |
| 2009/0048533 A1 | 2/2009 | Miller |
| 2009/0062624 A1 | 3/2009 | Neville |
| 2009/0082695 A1 | 3/2009 | Whitehead |
| 2009/0087249 A1 | 4/2009 | Flagle et al. |
| 2009/0088666 A1 | 4/2009 | Miller et al. |
| 2009/0112118 A1 | 4/2009 | Quick, Jr. et al. |
| 2009/0125062 A1 | 5/2009 | Amin |
| 2009/0137927 A1 | 5/2009 | Miller |
| 2009/0171242 A1 | 7/2009 | Hibner |
| 2009/0171243 A1 | 7/2009 | Hibner et al. |
| 2009/0204022 A1 | 8/2009 | Schwindt |
| 2009/0227893 A1 | 9/2009 | Coonahan et al. |
| 2010/0030020 A1 | 2/2010 | Sanders et al. |
| 2010/0063416 A1 | 3/2010 | Cicenas et al. |
| 2010/0152610 A1 | 6/2010 | Parihar et al. |
| 2010/0152611 A1 | 6/2010 | Parihar et al. |
| 2010/0160820 A1 | 6/2010 | Weikel, Jr. et al. |
| 2010/0160823 A1 | 6/2010 | Parihar et al. |
| 2010/0292607 A1 | 11/2010 | Moore et al. |
| 2010/0312140 A1 | 12/2010 | Smith et al. |
| 2010/0317995 A1 | 12/2010 | Hibner et al. |
| 2010/0317997 A1 | 12/2010 | Hibner et al. |
| 2010/0317998 A1 | 12/2010 | Hibner et al. |
| 2010/0324449 A1 | 12/2010 | Rostaing et al. |
| 2011/0004119 A1 | 1/2011 | Hoffa et al. |
| 2011/0105946 A1 | 5/2011 | Sorensen et al. |
| 2011/0152715 A1 | 6/2011 | Delap et al. |
| 2011/0160611 A1 | 6/2011 | Ritchart et al. |
| 2011/0208085 A1 | 8/2011 | Mccullough et al. |
| 2011/0224577 A1 | 9/2011 | Park |
| 2011/0295150 A1 | 12/2011 | Mccullough et al. |
| 2011/0313316 A1 | 12/2011 | Ranpura et al. |
| 2012/0065541 A1 | 3/2012 | Videbaek |
| 2012/0071787 A1 | 3/2012 | Reuber et al. |
| 2012/0095366 A1 | 4/2012 | Heske et al. |
| 2012/0130275 A1 | 5/2012 | Chudzik et al. |
| 2012/0184873 A1 | 7/2012 | Jorgensen et al. |
| 2012/0191009 A1 | 7/2012 | Hoon et al. |
| 2012/0203135 A1 | 8/2012 | Heske et al. |
| 2012/0215130 A1 | 8/2012 | Field et al. |
| 2012/0238905 A1 | 9/2012 | Heske et al. |
| 2012/0310109 A1 | 12/2012 | Almazan |
| 2012/0323120 A1 | 12/2012 | Taylor et al. |
| 2012/0323140 A1 | 12/2012 | Taylor et al. |
| 2012/0330185 A1 | 12/2012 | Coonahan et al. |
| 2013/0023789 A1 | 1/2013 | Anderson et al. |
| 2013/0023791 A1 | 1/2013 | Thompson et al. |
| 2013/0190648 A1 | 7/2013 | Videbaek |
| 2013/0197391 A1 | 8/2013 | Videbaek |
| 2013/0204161 A1 | 8/2013 | Videbaek et al. |

(56) References Cited

U.S. PATENT DOCUMENTS

| | | |
|---|---|---|
| 2013/0289441 A1 | 10/2013 | Videbaek et al. |
| 2016/0256138 A1 | 9/2016 | Videbaek et al. |

FOREIGN PATENT DOCUMENTS

| | | |
|---|---|---|
| DE | 3924291 A1 | 1/1991 |
| DE | 4041614 C1 | 10/1992 |
| DE | 3924291 C2 | 7/2000 |
| DE | 10034297 A1 | 4/2001 |
| DE | 10026303 A1 | 2/2002 |
| DE | 20204363 U1 | 5/2002 |
| DE | 20209525 U1 | 11/2002 |
| DE | 10235480 A1 | 2/2004 |
| EP | 0433717 A1 | 6/1991 |
| EP | 0890339 A1 | 1/1999 |
| EP | 0995400 A1 | 4/2000 |
| EP | 1074271 A2 | 2/2001 |
| EP | 1520518 A2 | 4/2005 |
| EP | 1579809 A1 | 9/2005 |
| EP | 1604615 A1 | 12/2005 |
| EP | 1665989 A2 | 6/2006 |
| EP | 1829487 A1 | 9/2007 |
| EP | 2095772 A1 | 9/2009 |
| EP | 2106750 A2 | 10/2009 |
| EP | 1569561 B1 | 10/2010 |
| FR | 1345429 A | 12/1963 |
| FR | 2739293 A1 | 4/1997 |
| GB | 2018601 A | 10/1979 |
| JP | 1-126957 A | 9/1987 |
| JP | H10508504 A | 8/1998 |
| JP | 2005530554 A | 10/2005 |
| JP | 2006509545 A | 3/2006 |
| JP | 2006528907 A | 12/2006 |
| JP | 2007502159 A | 2/2007 |
| WO | 9508945 A2 | 4/1995 |
| WO | 9628097 A1 | 9/1996 |
| WO | 9734531 A1 | 9/1997 |
| WO | 9825522 A1 | 6/1998 |
| WO | 9831285 A1 | 7/1998 |
| WO | 9835615 A1 | 8/1998 |
| WO | 9846290 A1 | 10/1998 |
| WO | 9933501 A1 | 7/1999 |
| WO | 0004832 A1 | 2/2000 |
| WO | 0030546 A1 | 6/2000 |
| WO | 0059378 A2 | 10/2000 |
| WO | 0172230 A1 | 10/2001 |
| WO | 0222023 A1 | 3/2002 |
| WO | 0232318 A1 | 4/2002 |
| WO | 02069808 A2 | 9/2002 |
| WO | 2005013830 A1 | 2/2005 |
| WO | 2006015302 A1 | 2/2006 |
| WO | 2007047128 A1 | 4/2007 |
| WO | 2007095330 A2 | 8/2007 |
| WO | 2007112751 A2 | 10/2007 |
| WO | 2008021687 A1 | 2/2008 |
| WO | 2008040812 A1 | 4/2008 |
| WO | 2008131362 A2 | 10/2008 |
| WO | 2010107424 A1 | 9/2010 |
| WO | 2010120294 A1 | 10/2010 |
| WO | 2011019343 A1 | 2/2011 |

* cited by examiner

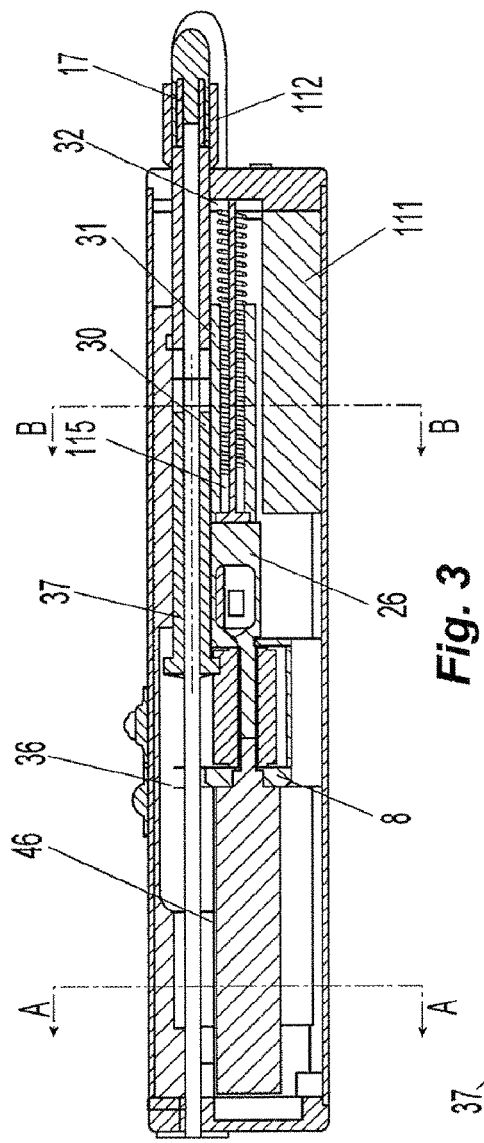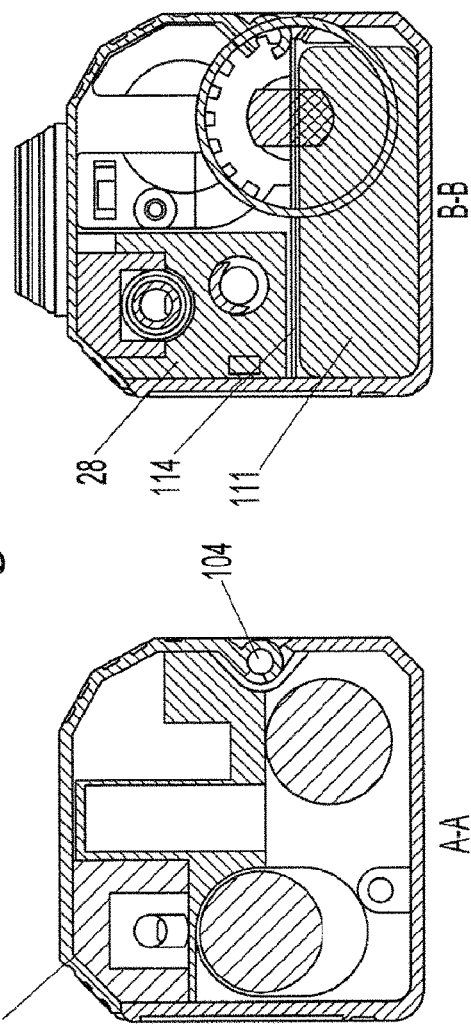

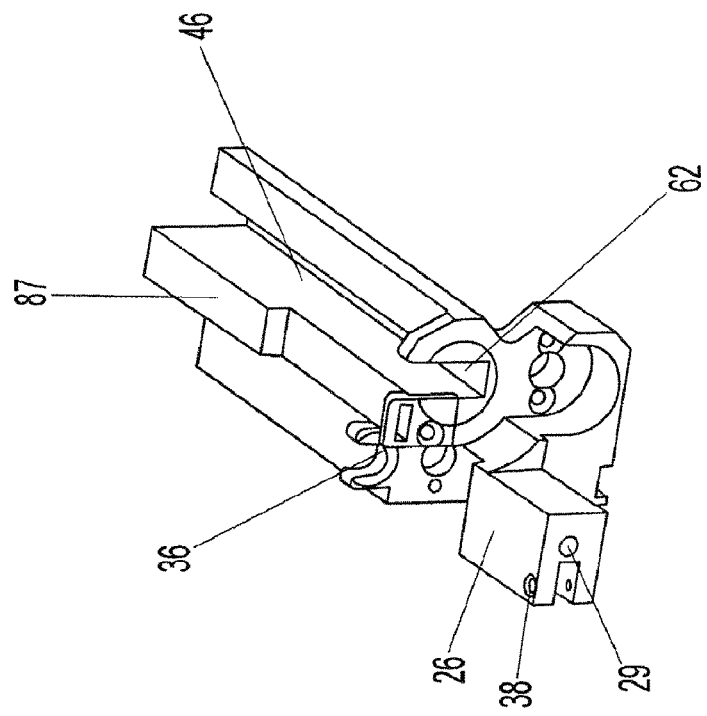
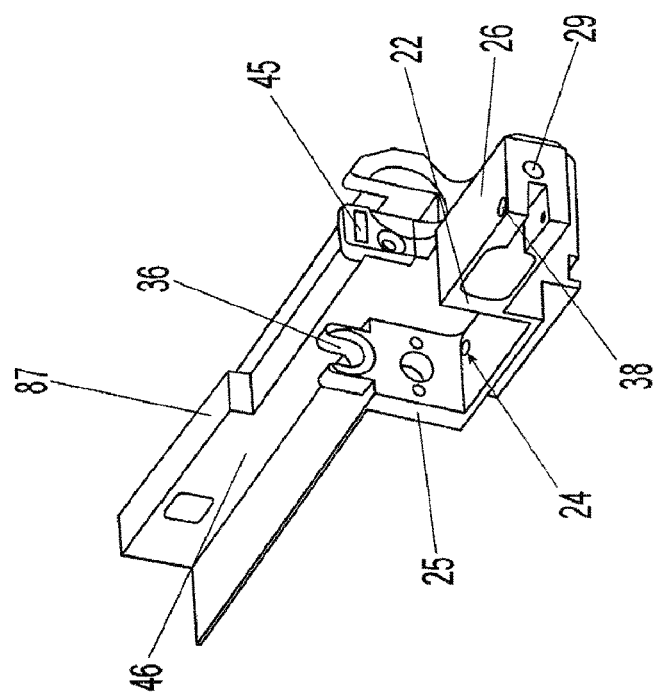
*Fig. 8b*
*Fig. 8a*

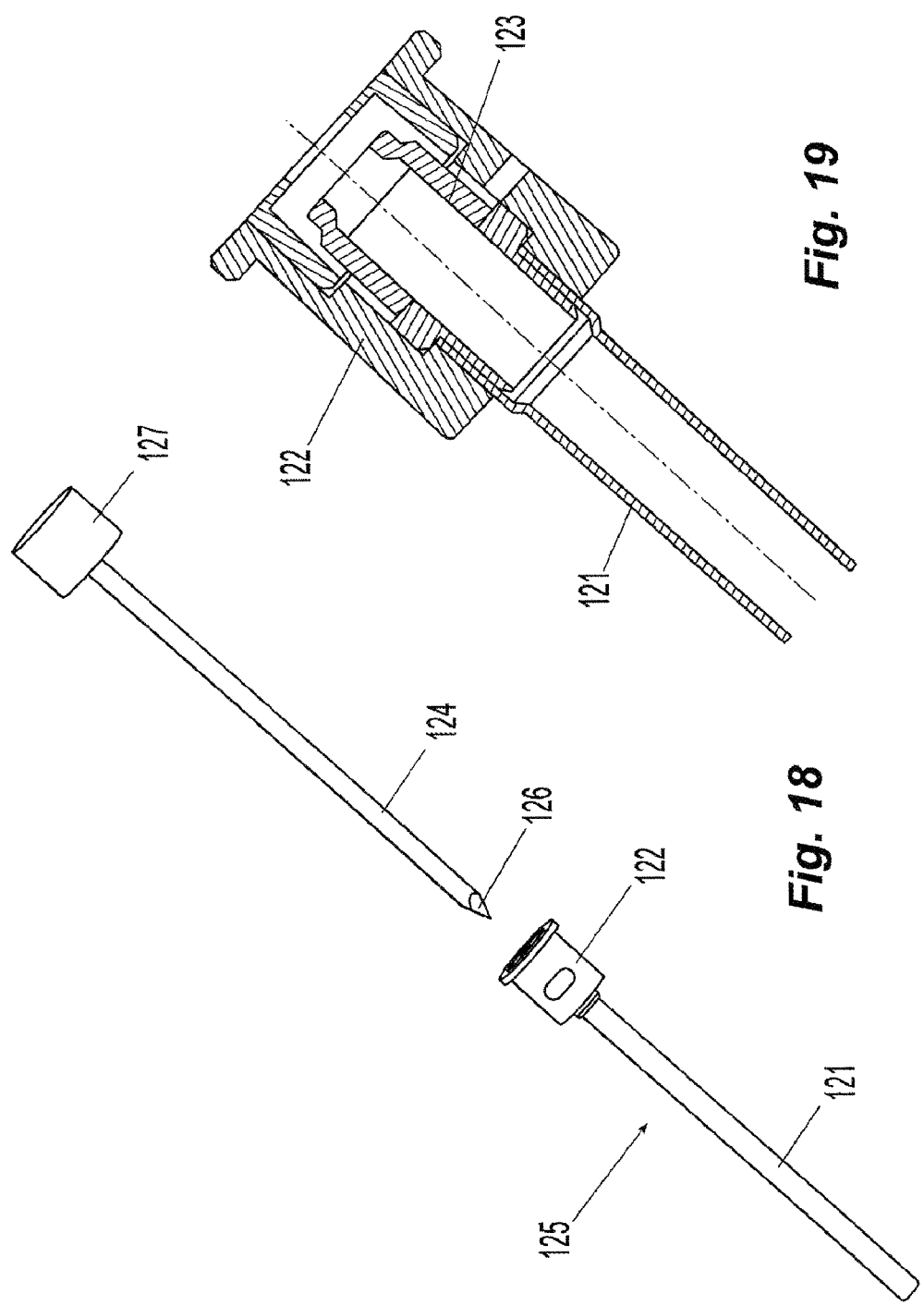

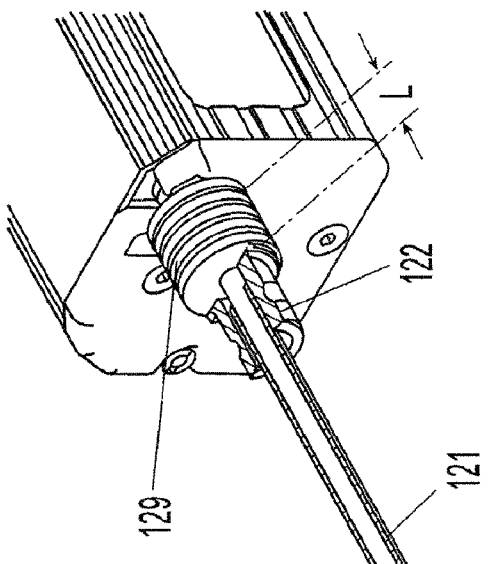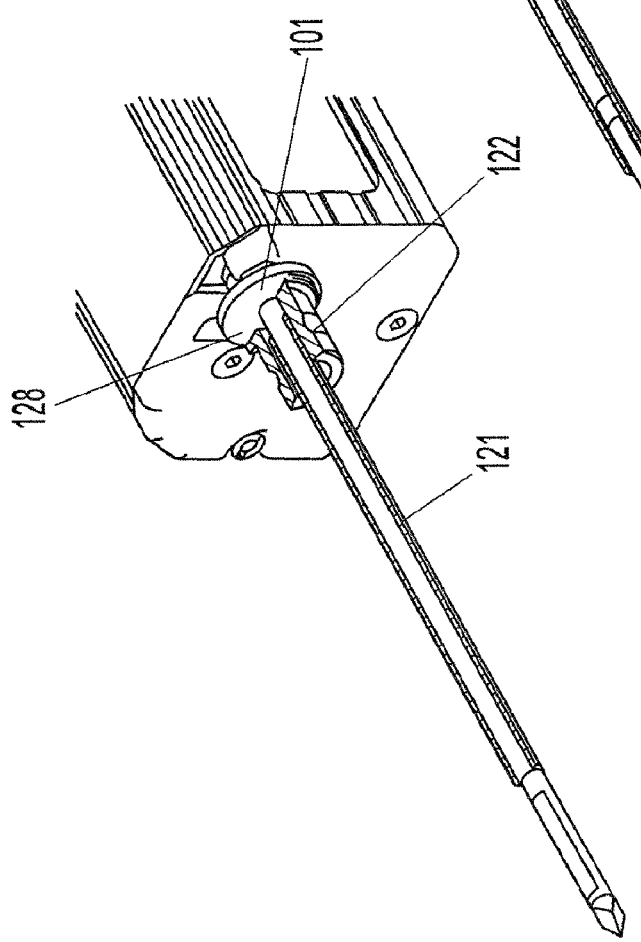

DISPOSABLE BIOPSY UNIT

CROSS-REFERENCE TO RELATED APPLICATIONS

This is a continuation of U.S. patent application Ser. No. 14/729,113, filed Jun. 3, 2015, which is a continuation of U.S. patent application Ser. No. 13/340,115, filed Dec. 29, 2011, now U.S. Pat. No. 9,072,502, which is a continuation of U.S. patent application Ser. No. 10/500,522, filed Apr. 6, 2005, now U.S. Pat. No. 8,109,885, which is a national stage application under 35 U.S.C. § 371 of International Application PCT/DE2003/00844, filed Mar. 17, 2003, which claims priority to DE20201363.0, filed Mar. 19, 2002, DE20204362.2,2, filed Mar. 19, 2002, DE20204361.4, filed Mar. 19, 2002, DE102121567.7, filed Mar. 19, 2002, DE10212139.7, filed Mar. 19, 2002, DE10212155.9, filed Mar. 19, 2002, DE20209525.8, filed Jun. 19, 2002, DE20209530.4, filed Jun. 19, 2002, DE20211934.3, filed Aug. 2, 2002, and DE20215962.0, filed Oct. 17, 2002.

MICROFICHE APPENDIX

None.

GOVERNMENT RIGHTS IN PATENT

None.

BACKGROUND OF THE INVENTION

1. Field of the Invention

The invention pertains to a biopsy device for taking of tissues samples, which consists of a hand piece, in which a hollow biopsy needle is inserted, wherein a portion of the biopsy needle protruding from the hand piece is introduced with its sampling chamber into the tissue being investigated and the tissue is sucked into the sampling chamber by vacuum and then separated by a sample separating mechanism and finally removed.

2. Description of the Related Art

A method and a device for cutting out tissue is already known from British Patent Publication No. GB 2018601A, in which the tissue in the biopsy needle is sucked into a cutting region under vacuum influence. In order to create a vacuum in the hollow needle, the hand piece in which the hollow needle is integrated is connected via lines to a vacuum generator situated outside of the hand piece. The cutting off of the sample is done via a cutting mechanism, which is arranged lengthwise-moveable in the hollow needle. The sample cut off is kept in the needle. After pulling the needle out from the tissue, the cut-off sample is flushed out from the tip of the needle; therefore, the hand piece is connected via other lines to devices situated outside the hand piece. The vacuum established in the hollow needle is regulated by control elements integrated in the lines.

Another biopsy mechanism is known from European Patent Publication No. EP 0890 339 A1, in which the sample is removed under vacuum influence. In the hand piece, in which the biopsy needle with cutting mechanism is integrated and inserted, the biopsy needle is connected via hose connections and lines to an external vacuum generator as well as control devices. The vacuum is brought up from below to the sample removing chamber via a channel molded onto the outer sheath of the biopsy needle. The separating device is arranged lengthwise moveable in the hollow space of the biopsy needle. By a rotary movement, combined with a manual lengthwise push, the separating device cuts the sample from the tissue. The sample is transported in the hollow channel of the separating device. A similar arrangement is also shown by U.S. Pat. No. 5,526,822, and here in particular various vacuum feed lines to the sample removal chamber are known, such as the arrangement for cutting mechanisms, in the hollow needle or coaxially as a cutting sheath, on the outside. In both biopsy mechanisms capable of removal of a sample under vacuum, the hand piece of the biopsy device is limited in its freedom of motion by at least one connection hose and/or supply cables to one or more external supply units; furthermore, the mechanisms for creating the vacuum are costly, especially in regard to the regulating mechanisms. The sample is cut out by rotating separation devices which can move lengthwise in the hollow needle chamber.

Furthermore, a suction biopsy device is known from German Patent No. DE 40 41 614 C1, which is fashioned as a manual device and which has a partial vacuum source as well as a biopsy cannula connection, which can be placed in rotation by a flexible shaft located outside the hand piece. A biopsy cannula fashioned as a hollow cannula can be mounted on the biopsy cannula connection, preferably having a revolving cutting edge sharpened at the distal end, along whose hollow channel a partial vacuum can be applied, by means of the partial vacuum source, which is configured as a piston and cylinder unit, once the hollow cannula has been positioned at a particular tissue point inside the body. A similar partial vacuum-assisted biopsy device can be found in International Publication No. WO 96/28097, which, though not specifying any hollow cannula placed in rotation, nevertheless has a syringe plunger arrangement located inside a manual device to create partial vacuum.

German Patent Publication No. DE 100 34 297 A1 describes, in contrast with the above suction biopsy arrangement with only a single hollow needle, a tissue removal endoscopy instrument, having a biopsy needle arrangement, which specifies a circumferentially sharpened hollow needle at its distal end and a hollow biopsy needle guided inside the hollow needle, wherein the internally guided biopsy needle has a recess for removal of a tissue sample at its distal end. Proximal to the hollow biopsy needle is a suctioning instrument for creating a partial vacuum. A removal of tissue occurs in that the biopsy needle arrangement is pushed in a joint position into a region of tissue being investigated, while the biopsy needle has a distal tip, which protrudes distally from the hollow needle for a length in order to facilitate the process of penetration of the biopsy needle arrangement into the tissue, on the one hand, and to prevent tissue from getting into the interior of the hollow needle, on the other hand. When the biopsy needle arrangement is suitably positioned inside the tissue, the hollow needle is pulled back proximally for a particular length, while the interior biopsy cannula remains in position and the recess is made free. The partial vacuum applied along the biopsy needle produces an active lowering or drawing of surrounding tissue parts into the recess. By controlled distal pushing of the hollow needle with its sharpened distal end beyond the biopsy needle, a portion of the tissue is separated and enclosed inside the recess of the biopsy needle. Then, by joint withdrawal of the biopsy needle arrangement, the separated tissue sample is removed from the body for examination purposes. The entire tissue removal process described above occurs in such a way that the needle movements and the application of partial vacuum are performed manually, individually and separated from each other. With German Patent Publication No. DE 100 34 297 A1, which is considered to be the closest state of the art, the vacuum biopsy device for removal of tissue is based on the problem of configuring the hand piece so that the sample removal sequence can be operated with one hand after being inserted by means of a coaxial cannula, or with no such cannula.

On the other hand, the biopsy needle arrangement described in International Publication No. WO 98/25522 enables a spring-operated relative motion between the hollow biopsy needle, located on the interior, and the outer hollow needle surrounding the biopsy needle. In this case as well, the biopsy needle is positioned distally to the sharpened distal tip of the hollow needle in order to take a sample, there being provided a partial vacuum source for supplying a partial vacuum through the hollow biopsy needle into the area of its recess, assisting the process of bringing in the tissue. The process of positioning the biopsy needle relatively and finally inside the region of tissue being investigated is done exclusively manually. Such a positioning leads only to unsatisfactory biopsy results, especially when investigating hard tissue regions.

Likewise, a vacuum-assisted biopsy device is described in US Patent Publication No. 2001/0011156 A1, which calls for a compactly configured hand device, in whose housing all drive elements necessary for propelling the needle of the biopsy needle arrangement are provided. However, a partial vacuum source is provided separate from the hand device, which can be connected via an appropriate supply line to the needle arrangement inside the hand device at a suitable connection location.

SUMMARY OF THE INVENTION

According to one aspect of the invention, a tension slide that is brought into cocked position by electric motor power against the action of a spring, the needle unit being arranged on the tension slide mounted in the hand piece, wherein the sample removal chamber is shot into the tissue after releasing the cocked tension slide. The vacuum pressure-generating device, as well as other control and supply devices, are integrated in the housing of the hand piece, and the connection element, from the biopsy needle to the vacuum pressure-generating unit, is arranged directly on the housing. The vacuum pressure-generating device comprises a controllable piston/cylinder unit, having a ventilation opening, so that excess pressure can be generated in the vacuum pressure-generating device for ejection of the sample. All drive units are electrically operated, and the drive unit for the tension slide may also be used as the drive unit for the cutting sheath. The hollow biopsy needle is surrounded by an exterior coaxial cutting sheath, and at the front side of the housing there is arranged a board for actuating the electronics, in which the tension slide release is integrated.

According to another aspect of the invention, by arranging all necessary devices in the hand piece, the hand piece is freely moveable; furthermore, high-speed electrical drive units are used exclusively, and the tension slide and the sample separating device are operated by the same drive unit. This produces a compact device, independent of other supply units. The drive units can be accommodated in a relatively small housing. Even the electronics and the operating and measuring instruments are arranged on the housing, or accommodated in it. This also applies to the power supply and the connection elements. It is therefore possible to bring together partial processes into a single control step and simplify the attendance, so that the attendance can be done with only one hand.

According to another aspect of the invention, for an especially simple and reliable configuration of the vacuum generating device, the use of a piston/cylinder unit with ventilation possibility to create the vacuum and the excess pressure works well. Especially advantageous is the use of a familiar syringe/plunger unit, with a ventilation opening arranged in addition in the upper part of the syringe body, which is opened in order to dissipate the vacuum by further retraction of the syringe plunger. By controlling the spindle drive unit of the plunger spindle, the same plunger/syringe unit can be switched as needed from generating a vacuum to generating an excess pressure, using, to dissipate the vacuum, a ventilation opening arranged in the upper part, through which air flows in, and is compressed in the following step.

According to another aspect of the invention, in order to control the motion of the plunger, especially in regard to switching from creation of a vacuum to dissipation of a vacuum and generating of excess pressure, a spindle drive with electric DC motor with secondary reduction gearing has proven to be advantageous as the drive unit. The measured speed of revolution of the motor represents a direct measure of the lengthwise displacement of the plunger. Since this is a high-speed DC motor, whose take-off speed is considerably reduced by a reduction gearing, the lengthwise motion of the spindle can be controlled exactly. The length of the spindle travel and thus the magnitude of the vacuum and the excess pressure can be set with appropriate setpoint values in the control electronics, e.g., the speed of revolution of the motor.

According to another aspect of the invention, since a sterile biopsy needle is used for each patient, it has proven to be advantageous to separate the sterile parts from other merely disinfected parts that are firmly connected to the hand piece. For this reason, it is convenient to design the vacuum pressure-generating device, the biopsy needle with cutting sheath and the parts connected to the biopsy needle and cutting sheath, such as the biopsy needle carrier, the drive elements and plastic piece including connection element and guide roller as an independent, easily inserted and removed sterile insert element. The space for the insert element is separated from the other drive elements by covers, for reasons of cleaning of the hand piece.

According to another aspect of the invention, for sake of simplicity, the flexible connection element is fashioned as a flexible hose, so that it can adapt to the displacement travel of the tension slide. In order to allow for twisting of the hose relative to the biopsy needle at the proximal end, an additional rotary mounted plastic piece is arranged in the plastic piece firmly connected to the biopsy needle, to which the hose is attached. In order to enable a lengthwise movement of the gear connected to the spindle casing for driving of the spindle casing, e.g., when the tension slide is released, a toothed roller is provided as the drive unit. In order to provide for a cocking of the tension slide via the biopsy needle carrier by turning the cutting sheath, the gear at the end face of the threaded spindle casing is supported against a holder of the base block during the cocking process, so that the biopsy needle carrier moves to the right, while the cutting sheath maintains its position.

According to another aspect of the invention, the locking of the tension slide has a double-arm lever, whose one arm engages under spring pressure with the recess of the tension slide. In order to allow for use of the tension device for different biopsy needles with different insertion depths, e.g., 15 to 25 mm, it is only necessary to adapt the length of the engaging lever and use appropriate settings in the electronics, for example. The plastic piece joined to the biopsy needle enables a turning of the sample removal chamber by means of a knurled disk. The biopsy needle can be locked in the desired position by the interaction of the polygon of the plastic piece and the biopsy needle carrier. A notch made in the knurled disk shows the user the radial position for the opening of the sample removal chamber.

According to another aspect of the invention, the cross section of the hollow biopsy needle is limited by a narrowing, a stuffing, or a lip at the sample removal chamber. This narrowing is around 60-75% of the height and closes off the upper open part of the sample removal chamber from above. This narrowing in front of the sample removal chamber has the effect that the vacuum sucks in the tissue being investigated from the bottom—upon opening of the sample removal chamber—(i.e., upon retraction of the cutting sheath). The narrowing in addition prevents tissue from getting into the rear part of the hollow needle space. When the sample is ejected, the narrowing produces a pressure increase in the sample removal chamber, which improves the cleaning effect, especially in the sample removal chamber. By applying the vacuum, the tissue of the sample is sucked into the interior of the sample removal chamber and clings more or less to the inner wall. For better adhesion, additional means can be provided in the interior of the sample removal chamber. Since the cutting sheath is arranged on the outer diameter of the biopsy needle and thus the separation of the tissue occurs externally, the tissue clinging to the inner space is not detached from the inner wall by the cutting mechanism, thanks to the external arrangement of the cutting sheath. Furthermore, the tissue cannot get into the cavity of the rotating cutting mechanism and get stuck inside. Guiding of the cutting sheath with its round cross section on the outer side of the biopsy needle with its round cross section has the advantage that no twisting (turning) of the sample can occur by the cutting rotation of the cutting mechanism, thus fulfilling a major requirement for the evaluation of the tissue by the pathologist. In order to achieve a good adhesion of the sample in the inner space without impairing the fill ratio, the sample removal chamber is configured so that approximately 25% of its cross section is open for suctioning in the sample, i.e., the larger portion of the circumference is closed.

According to another aspect of the invention, the arrangement of the coaxial cutting sheath on the outside also has the effect that a larger sample can be removed than when the cutting sheath is arranged on the inside. Since the sample is ejected with assistance from a pressure built up from the sample removal chamber, no damage to the tissue occurs when taking the tissue out. Thanks to the central arrangement of the base block at the center of the inner chamber of the housing, the housing itself is protected against transverse forces produced by the drive elements. Furthermore, it is easy to replace the drive units, as well as the tension slide, since it is only necessary to loosen the connections to the housing for this. It is also advantageous that the impacts produced by the plastic tension slide are absorbed by the base block.

According to another aspect of the invention, the storing of the biopsy needle/cutting sheath in a biopsy needle carrier made of plastic has the advantage, among others, that the molded-on sliding surfaces enable a trouble-free sliding on the opposing surfaces of the base block and the molded-on block. The biopsy needle carrier transmits the forces from the spindle drive of the cutting sheath to the tension slide. Since the spindle drive thrusts against the holder of the base block when the tension slide changes position and it can slide freely when the tension sheath is rotated (the gear can slide axially in the toothed roller), the drive unit can be used for both motion sequences (tensioning of the tension slide, opening and closing of the sample removal chamber by means of the cutting sheath). The miniature switch integrated in the housing end piece, which turns the power supply off and on by the closing of the housing cover with the vacuum pressure-generating device inserted, as well as the retaining tabs arranged on the biopsy needle carrier, are safety mechanisms which prevent a tensioning of the tension slide when the housing cover is open. Furthermore, an opening of the housing cover when the needle is under tension will be precluded.

According to another aspect of the invention, the guide roller, mounted in the end cover of the housing with the biopsy needle and cutting sheath passing through it, cooperates with the cannula which has been inserted into the tissue. Because a seal element is placed on the proximal end of the previously mounted coaxial cannula, interacting with the cutting sheath, air is prevented from getting in between the cannula and the cutting sheath. The guide roller placed on the cannula prevents the inner housing from getting dirty and prevents the nonsterilized hand piece from touching the coaxial cannula. The board arranged on the hand piece with integrated light-emitting diodes and switches, as well as icons, accomplishes a simple operator guidance. The cover plate can also be used as a carrier for miniature switches or photocells. The insertion aid enables easier insertion of the sterilized replacement element.

According to another aspect of the invention, in order to make sure that the tissue is reliably cut through when the sample removal chamber is closed, the cutting sheath travels by approximately 2 mm out toward the tip of the needle, beyond the distal end of the sample removal chamber. To prevent operator error, the sequences "cocking of the tension slide" and "ejection of sample" are provided with delay circuits. To enhance the safety, it may be advisable to select a different color for the light-emitting diodes in the case of processes taking place in the tissue, such as "separate the sample", than that for processes taking place outside the tissue, such as "eject the sample".

According to another aspect of the invention, when using a coaxial cannula in which the needle unit is inserted, so as to achieve an exact positioning, for example, one must make sure that no air can get in between the outer circumference of the needle and the inside of the coaxial cannula when a vacuum is produced. Therefore, a seal element is provided at the proximal side of the coaxial cannula tube. Since the depth of insertion of the needle unit is dictated by the cocking distance of the tension slide, unless means are provided in the hand piece for different depths of insertion, the use of spacing pieces between the coaxial cannula and guide roller has proven to be especially advantageous. The spacing piece is strung onto the needle unit and sits distally on the proximal end of the coaxial cannula, and proximally on a guide roller arranged in the hand piece. As a result, for the same insertion length dictated by the device, the depth of penetration is reduced by the length of the spacing piece, resulting in easier production conditions.

The invention, in one form thereof, is directed to a disposable biopsy unit for removable coupling to a handheld biopsy driver. The disposable biopsy unit includes a biopsy needle unit and a pump. The biopsy needle unit includes a carrier, a biopsy needle and a cutting sheath. The carrier is configured to mount the biopsy needle and the cutting sheath. The biopsy needle has a sample removal chamber and a longitudinal axis. The cutting sheath is coaxially arranged with the biopsy needle. The cutting sheath is configured to move along the longitudinal axis relative to the biopsy needle. The pump has an elongate cylinder and a plunger. With reference to the component arrangement of FIG. 1, the plunger is configured to be movable inside the elongate cylinder in a first direction from a proximal end of the elongate cylinder to a distal end of the elongate cylinder to generate a vacuum and configured to be movable inside the elongate cylinder in a second direction from the distal end of the elongate cylinder to the proximal end of the elongate cylinder to build up pressure. The proximal end of the elongate cylinder is coupled in fluid communication with the biopsy needle.

The invention, in another form thereof, is directed to a disposable biopsy unit for removable coupling to a handheld biopsy driver. The disposable biopsy unit includes a carrier, a biopsy needle assembly mounted to the carrier, and a pump. The pump includes an elongate cylinder. The elongate cylinder is connected in fluid communication with the biopsy needle assembly. A plunger is configured to move inside the elongate cylinder. The plunger has a rack. A toothed crown nut is configured to mesh with the rack. The tooth crown nut is configured to rotatably engage an end portion of the elongate cylinder, and configured such that the plunger is translated in the elongate cylinder to generate one of vacuum and pressure as the toothed crown nut is rotated.

BRIEF DESCRIPTION OF THE DRAWINGS

The invention shall now be described as an example by means of sample embodiments making reference to the drawings, without limiting the general notion of the invention.

FIG. 3 shows a lengthwise section A-A through the biopsy needle of FIG. 1.

FIG. 4 shows a cross section A-A in FIG. 3 (left housing part).

FIG. 5 shows a cross section B-B in FIG. 3 (right housing part).

FIG. 8a shows a base block in X-axis viewed from front (perspective).

FIG. 8b shows a base block in X-axis viewed from behind (perspective).

FIG. 11e shows a cross section A-A in FIG. 11a.

FIG. 18 shows a coaxial cannula and spike (exploded view).

FIG. 19 shows a section through the cap of a coaxial cannula.

FIG. 20 shows a coaxial cannula with inserted needle unit.

FIG. 21 shows a coaxial cannula with inserted needle unit making use of a spacing piece.

DETAILED DESCRIPTION OF THE INVENTION

Figure 1:
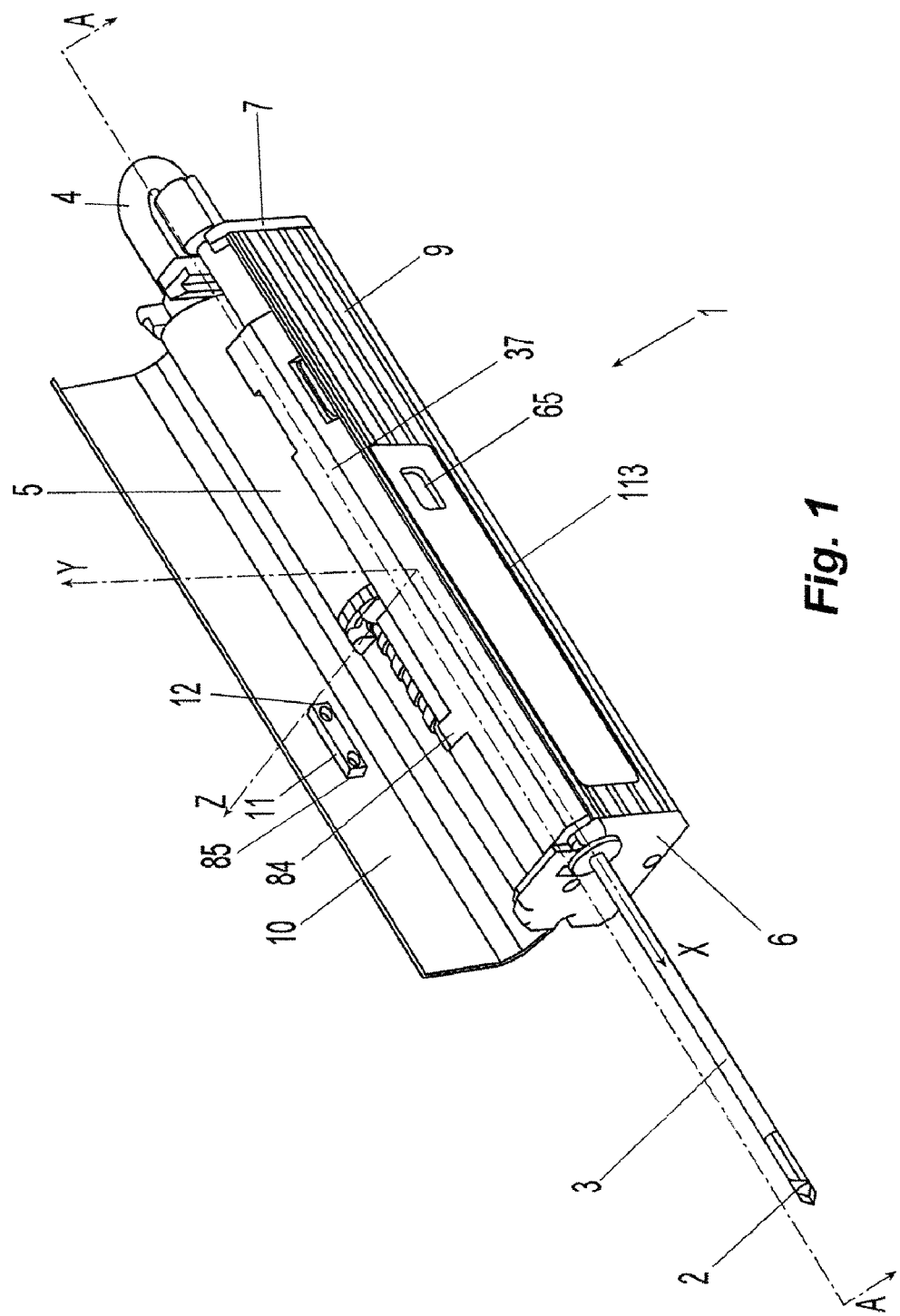
FIG. 1 shows a biopsy device with open housing cover (perspective view).

The following detailed description should be read with reference to the drawings, in which like elements in different drawings are identically numbered. The drawings, which are not necessarily to scale, depict selected preferred embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Integrated in the housing interior of a hand piece 1 are all devices required to perform a vacuum biopsy (FIG. 1), so that no cables or lines are required going from the housing of the hand piece to other external supply devices. Thus, the hand piece 1 constitutes a complete vacuum biopsy device, which is freely moveable in all directions.

From the distal part of the left end cover 6 protrudes the distal part of the hollow biopsy needle 2 with the cutting sheath 3 surrounding it coaxially, which is required to remove the tissue sample. Usually, a coaxial cannula is placed in the tissue, into which the biopsy needle 2 with cutting sheath 3 is introduced. Outside the right end cover 7 of the housing there is arranged a connection element 4, e.g., a transparent flexible hose, which connects the vacuum pressure-generating device 5, arranged in parallel with the biopsy needle, to the interior cavity of the biopsy needle 2.

Figure 2:
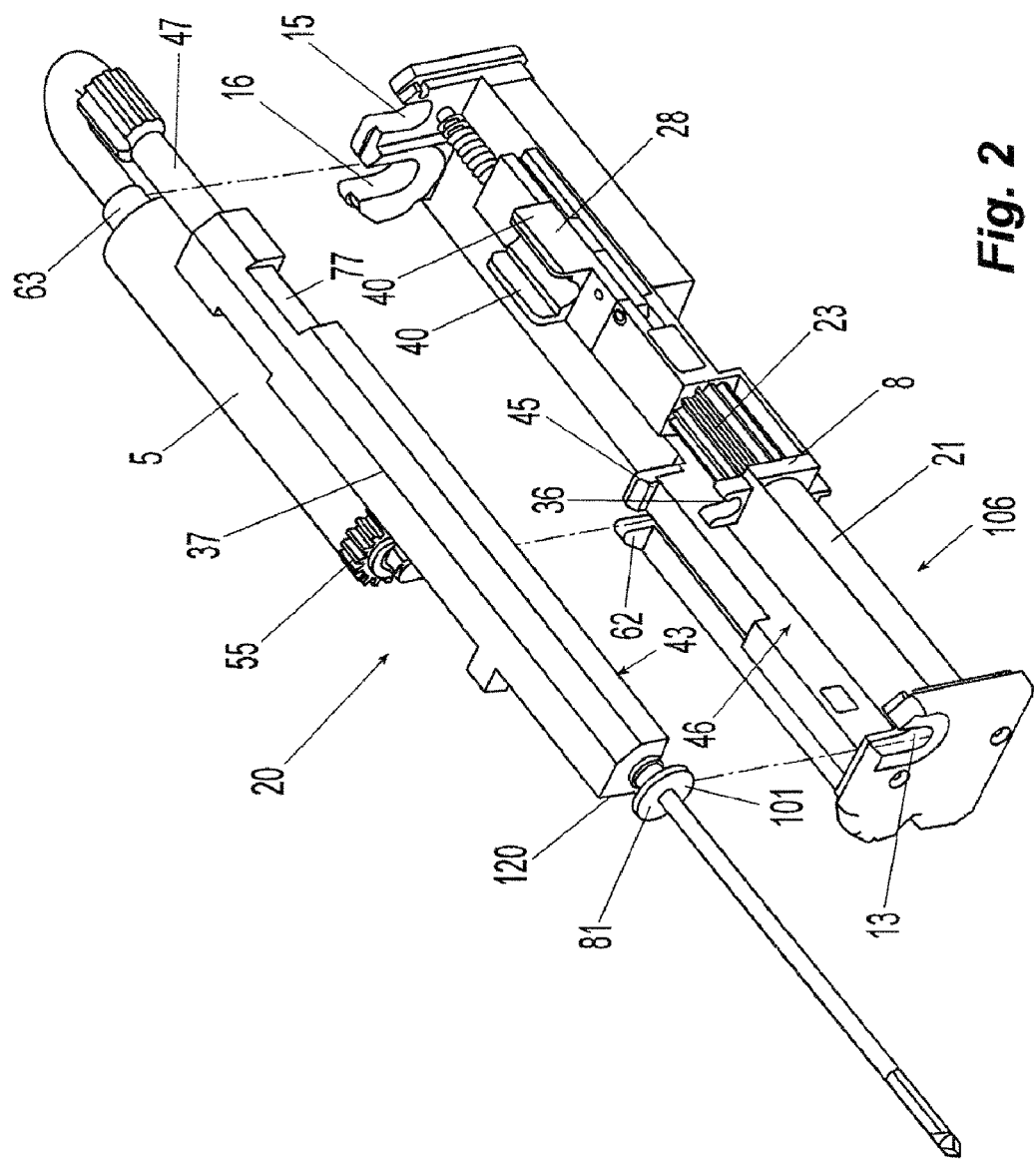
FIG. 2 shows a unit of the biopsy device which is fixed to the housing (without bottom of housing and cover) and the replaceable biopsy unit; shown separately (perspective view).
Figure 7:
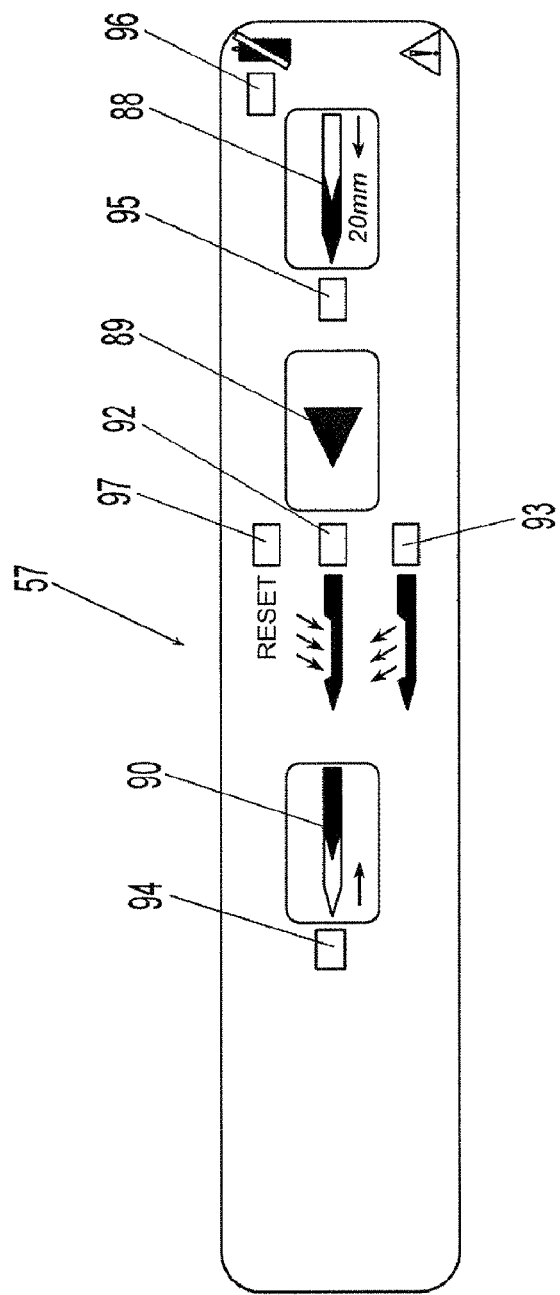
FIG. 7 shows a front side of board.

The hollow connection element 4 is situated in immediate proximity to the end cover 7 of the housing. The biopsy needle with cutting sheath and additional elements, arranged in a biopsy needle carrier 37, forms together with the connection element 4 and the vacuum pressure-generating device 5 an element 20, easily inserted or taken out at the top, which is replaced as necessary (FIG. 2). The housing cover 10 is opened for this purpose. As FIG. 2 in particular shows, the biopsy device can be divided into parts which are firmly connected to the housing (disinfected parts) and a removable element 20 (sterile part). While the parts firmly connected to the housing are merely disinfected, the removable element 20 comes in a sterile package and can be replaced as necessary, especially for each new patient.

In the sample embodiment described hereafter, the vacuum pressure-generating device is arranged in parallel with the biopsy needle. However, in the scope of the invention, the vacuum pressure-generating device can also be arranged lying in the axis of the biopsy needle or the hand piece; neither does it require its own connection element, if for example it is mounted directly on the end of the biopsy needle.

Between the left and right end covers 6, 7 of the housing is the lower piece 9 of the housing and a housing cover 10 which is hinged in the end covers of the housing, with a locking latch 11. By means of tie rods or screws, which are partly screwed into a base block 8, the lower piece 9 of the housing is clamped between the end covers 6, 7, or it is joined to the base block 8. The housing cover 10 can swivel about an axis secured in the end covers 6, 7 of the housing. The housing cover 10 is closed before the biopsy mechanism is used; the inner contour of the housing cover corresponds to the outer contour of the biopsy needle carrier 37, which will be described more precisely hereafter. Approximately at the center of the interior space of the housing is arranged the base block 8, which is firmly connected to the lower piece of the housing, for example, by fixation elements and/or by a screw connection. The base block 8, which extends not only in the lengthwise axis from the middle to the left, but also across the entire transverse surface, is connected to the drive elements for the vacuum pressure-generating device 5, the cutting sheath 3 and the cocking mechanism for the tension slide 28, on which the biopsy needle carrier 37 is mounted. Furthermore, the base block 8 has a holder 36, open at the top, for the biopsy needle/cutting sheath, and an additional insert element 62 for the vacuum pressure-generating device.

In order to specify the position of the individual elements, as well as the position of the individual parts, especially in the interior of the housing, a coordinate scale has been drawn in FIG. 1, the midpoint of the coordinates lying at the center of the base block 8 (FIG. 1). Accordingly, for the following description and for the claims, movement indicated in the direction of the X-axis is considered left (distal) and movement indicated away from the X-axis is considered right (proximal). For the other coordinates, movement in the direction of the Y-axis is considered top, movement away from the Y-axis is considered bottom, movement in the direction of the Z-axis is considered rear, and movement away from the Z-axis is considered forward (FIG. 1). Thus, the coordinate system divides the interior of the housing and the other references into left and right, forward and rear, and top and bottom.

Making reference to these remarks, in the bottom, front, left part of the housing interior are found the joint actuating mechanisms 106 for the cocking mechanism and the cutting sheath, and in the bottom, rear, left part of the housing is the actuating mechanism 105 (FIG. 13) for the vacuum pressure-generating device 5. In the bottom right part is accommodated the energy supply for the actuating motors and the other electrical parts, such as for the control and/or monitoring elements; preferably, batteries or a storage battery 111 are used for this, e.g., a 7.2 V lithium ion battery, 1 Ah. The forward, right, top interior space of the housing lying above the battery compartment is utilized mainly for the tension slide 28 with locking piece (FIG. 5); this is connected to a block 26, which is part of the base block 8. The battery compartment is sealed on top by a separation plate 114.

In the uppermost front part of the housing interior there is arranged a biopsy needle carrier 37, which can be inserted into and taken out from the U-shaped insert holder 36 of the base block 8, which is open at the top, and the bracket 40 arranged on either side of the tension slide 28 and pointing upward; the biopsy needle/cutting sheath unit with actuating parts is moveably mounted in this, extending for almost the entire length of the hand piece. This means that, in the uncocked state, the left end surface of the biopsy needle carrier 37 lies against the left end cover 6 of the housing, and in the cocked state the right end surface lies against the right end cover 7. "Almost the entire length" means that the biopsy needle carrier is at least shorter by the distance required in the interior of the housing for the cocking sequence. If the cocking distance of the tension slide is 20 mm, for example, the biopsy needle carrier must be able to move by this amount. In general, the cocking distance is between 15 and 25 mm, depending on the biopsy needle used. It is therefore advisable to design the interior for the longest possible cocking distance.

Figure 9B:
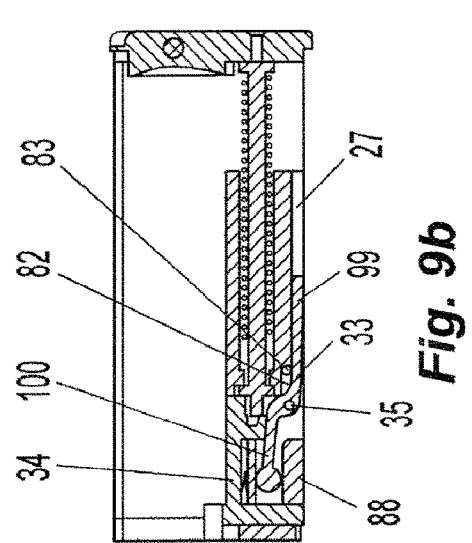
FIG. 9b shows a locking mechanism in the uncocked condition.
Figure 10B:
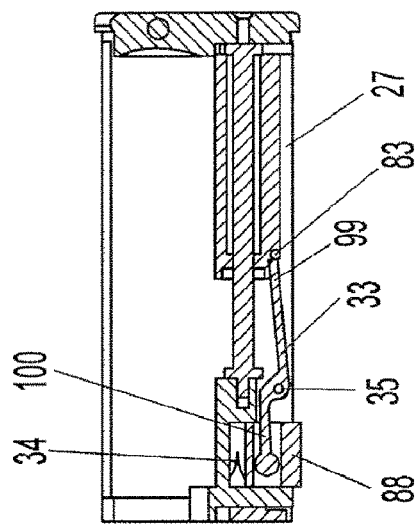
FIG. 10b is the same as FIG. 9b, but in the locked condition.

The cocking device (situated right front) itself consists of a tension slide 28, placed on a bolt 30, the bolt screwing into the base block 8. The bolt 30 has a spiral spring 31 surrounding it. The locking device (see especially FIGS. 9b and 10b) of the tension slide is secured to the block 26. In the top, rear, right interior of the housing is accommodated the vacuum pressure-generating device 5 with parts of the actuator; the actuating motor with reduction gearing for the vacuum pressure-generating device is located in the left, bottom, rear area of the housing interior.

The hand piece, and also in particular the biopsy needle or the vacuum pressure-generating device, are not connected either by cable or hose lines to additional supply units situated outside of the housing hand piece. Therefore, the mobility and maneuverability is not impaired either by lines or by cables. The housing cover, the bottom piece of the housing, the end covers of the housing and the base block consist preferably of aluminum.

The hand piece 1 consists, as already specified, of a housing, which is formed from a housing lower piece 9 with side walls raised to different height, the housing cover 10 adapted to the lower piece of the housing with lengthwise moveable locking latch 11, and the two end covers 6 and 7. The lower piece of the housing is joined to the two end covers by tie rods or screws, e.g., made of iron, which are partly screwed directly into the base block 8. The housing is around 200 mm in length, the end covers have approximately square cross section, roughly 40×40 mm (FIG. 2). The housing cover 10 can swivel about an axis 104, which is secured in the end covers 6, 7; boreholes 14 in the end covers are used for this. The dog 12 of the locking latch 11 can be pushed into the recess 45 of the base block 8 to close the housing cover.

Figure 6:
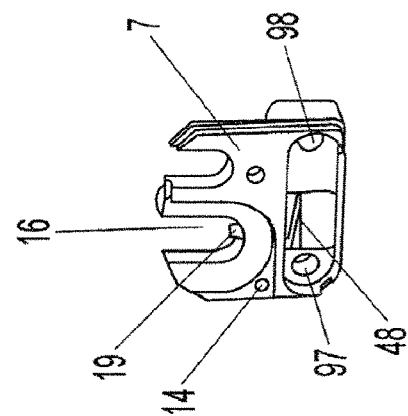
FIG. 6 shows a right housing end cover (inside) with integrated miniature switch.

The left end cover 6 has, in the upper forward part, an upward open U-shaped passage 13 for the forward protruding part of the biopsy needle/cutting sheath 2, 3 and the guide roller 81 mounted thereon. The rear end cover 7 of the housing has two upward open U-shaped passages 15, 16. The passage 15 corresponds to the passage 13; it receives the end of the plastic part 47, with round cross section, mounted on the hollow biopsy needle. In passage 16 is inserted a connection piece 63 for the vacuum pressure-generating device (FIG. 2). An additional plastic part 112, inserted in the plastic part 47, has a plug 17 which is used to connect the connection element 4 to the outlet connector 64 of the vacuum pressure-generating device. The inner cavity of the biopsy needle is connected continuously to the cavity of the plunger/cylinder arrangement and the cavity of the vacuum pressure-generating device. The connections are configured such that neither can air get into the system from the outside nor can air flow out when excess pressure prevails; thus, the connection points are air-tight. As FIG. 6 shows in particular, a miniature switch 18 is integrated in the passage 16 of the right end cover 7 at the bottom side, whose switch pin 19 protrudes into the passage. As soon as the connector 63 of the vacuum pressure-generating device is inserted in the passage and the housing cover is closed, the switch pin 19 of the miniature switch 18 is pressed downward and the miniature switch 18 allows current to flow. Terminals for hooking up a charger can be built into the passages 97, 98 of the right end cover 7.

At the front side of the bottom piece 9 of the housing there is a surface 113 provided for the board with the operating and monitoring elements (FIG. 1). The board 57 secured to the housing is designed as an independent component, which is glued, for example, onto the surface 113 of the bottom piece 9. This board 57 is connected by lines to other electronic components arranged in the housing, and to the power supply. The board contains in particular switches for the operation and diodes for the monitoring. The activating button 88 for mechanical triggering of the cocked tension slide protrudes through a recess 65 in the bottom piece of the housing and the board.

When configuring the operating and monitoring elements consideration was given to the difference between the cocking sequence of the tension slide and the triggering of the tension slide, on the one hand, and the performance of the biopsy, such as the cutting out of the sample, as well as the removal of the sample with the ejection of the sample, on the other hand. Accordingly, the activating button 88 (trigger) for the tension slide has been placed at the right and the cocking button 90 for cocking the tension slide is at left. The program button 89 for performing the biopsy is in the middle. It is necessary to press the program button for three functions. The first function, start or reset, is indicated by the reset diode 91, while the sample removal diode 92 arranged underneath indicates the opening and closing of the sample removal chamber when removing the sample. The lowermost eject diode 93 indicates the ejection of the removed sample. The cocking diode 94 indicates the cocking of the tension slide; the locking diode 95 indicates the locking of the tension slide. The battery charge diode 96 indicates the charge condition of the battery or storage battery. The diodes are switched so that the diode blinks while performing the particular sequence and after completion of the sequence the diode remains lit. When there are two possible choices, both diodes are lit. The operator is then free to make a choice. The mode of operation and possibility of control shall be examined more closely in detail when describing the sequence. Symbols (icons) at the margin symbolize the individual processes.

To improve the operating safety it may be advisable to outfit individual automated sequences with delay circuit. In particular, it has been found that the processes of "cocking of the tension slide" by pressing the cocking button 90 and "ejection of sample" by pressing the program button 89 are provided with delay circuits of around 1.2-1.5 seconds to improve the operating safety. Furthermore, the operating safety is improved when the light-emitting diodes indicating the individual processes have different colors for processes outside and processes inside the tissue.

A perspective representation of the base block 8 (looking from the front in the direction of the X-axis) is shown by FIG. 8a; the base block 8 is shown from the rear in the X-axis by FIG. 8b (both of them perspective views). The base block 8 can be divided into two halves, looking in the lengthwise direction; the front part serves to secure the joint actuation for the cutting sheath and tension slide, and also in its upper part to mount the biopsy needle carrier (FIG. 8a); the rear part serves to secure the actuation for the vacuum pressure-generating device and to mount one side of the vacuum pressure-generating device (FIG. 8b). Between the two actuating motors 21, 58, beneath the center rib 87, is arranged a central electronic board. The base block 8 has in its left front part a U-shaped space 24, in which is installed a toothed roller 23, driven by the gear motor 21. For this, the take-off shaft of the gear motor is mounted or inserted in an opening in the wall 25 of the base block 8. The toothed roller 23 is mounted on the take-off shaft and secured to it, for example, by means of a screw, so that it cannot turn or shift. At the other end, the toothed roller 23 is mounted in the wall 22 of the base block 8. The actuating motor used is a DC motor with a speed of around 11000 rpm. The DC motor is connected to a planet gear with high reduction ratio, on whose take-off shaft the toothed roller 23 is mounted.

An additional block 26 is molded on the wall 22, pointing to the right, which accommodates both the swiveling double lever 33 for the locking process and also serves to fasten the bolt 30 for guiding the tension slide 28. The bolt 30 is screwed into the threaded borehole 29. During the cocking process, the tension slide 28 moves to the right on the bolt 30 and the separating plate 114 is arranged underneath. The spiral spring 31 arranged on the threaded bolt 30 is compressed during the cocking process. At one end, the spiral spring thrusts against an end piece 32 of the threaded bolt or directly against the end cover 7 of the housing; the other end of the spiral spring thrusts against the end of the guide borehole 115 of the tension slide.

Figures 9A, 10A:
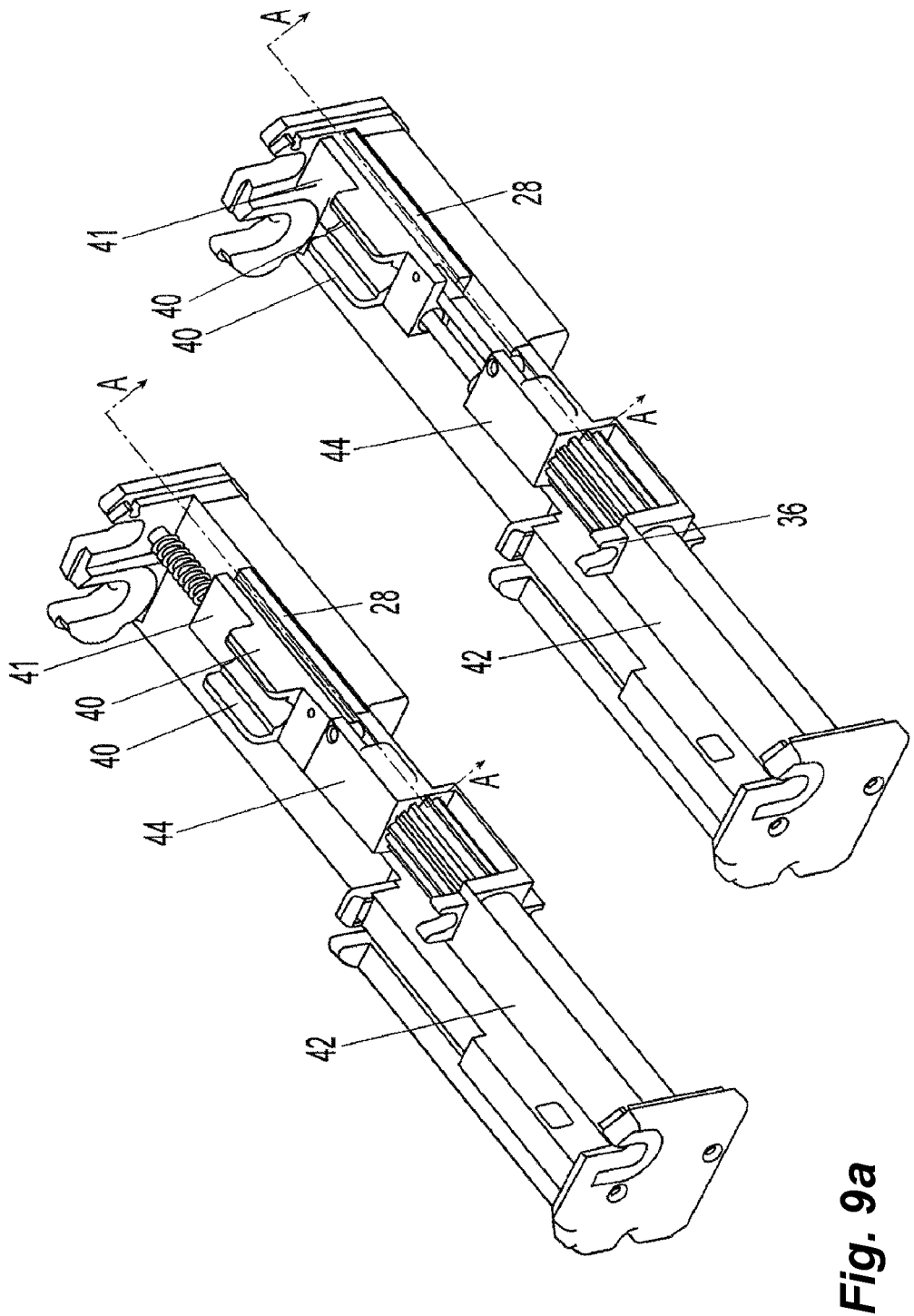
FIG. 9a shows a unit of the biopsy device that is fixed to the housing (without housing cover or bottom) in the uncocked condition.
FIG. 10a is the same as FIG. 9a, but with the tension slide in cocked position.
Figure 11A:
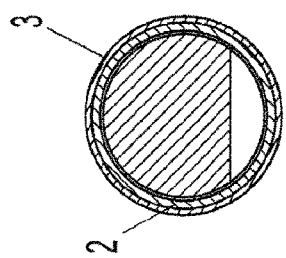
FIG. 11a shows a side view of a biopsy needle tip.
Figure 11B:
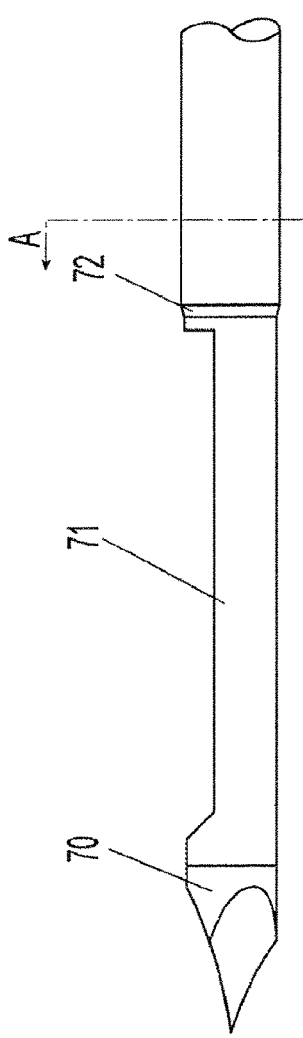
FIG. 11b shows a lengthwise section through FIG. 11a (sample removal chamber opened).
Figure 11C:
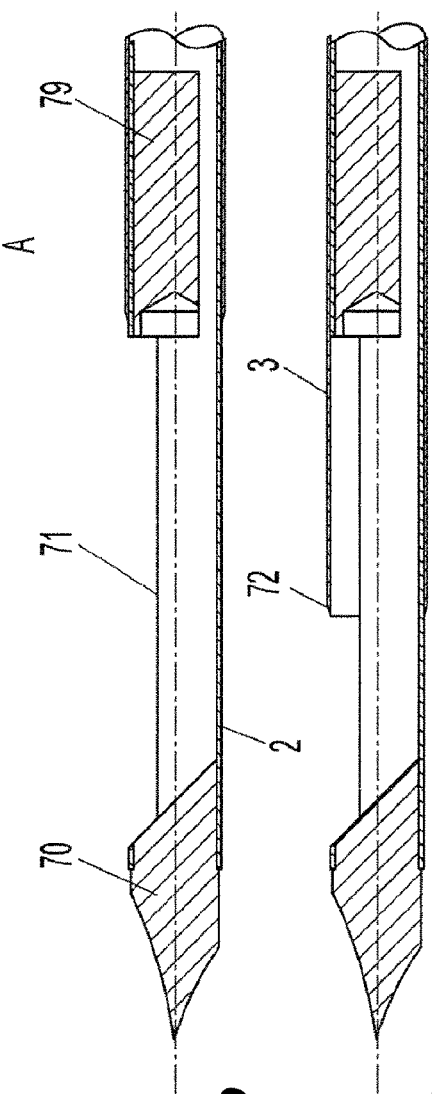
FIG. 11c is the same as FIG. 11b, but (sample removal chamber half open).
Figure 11D:
FIG. 11d is the same as FIG. 11b, (sample removal chamber closed by cutting sheath).
Figure 11E:
Figure 12:
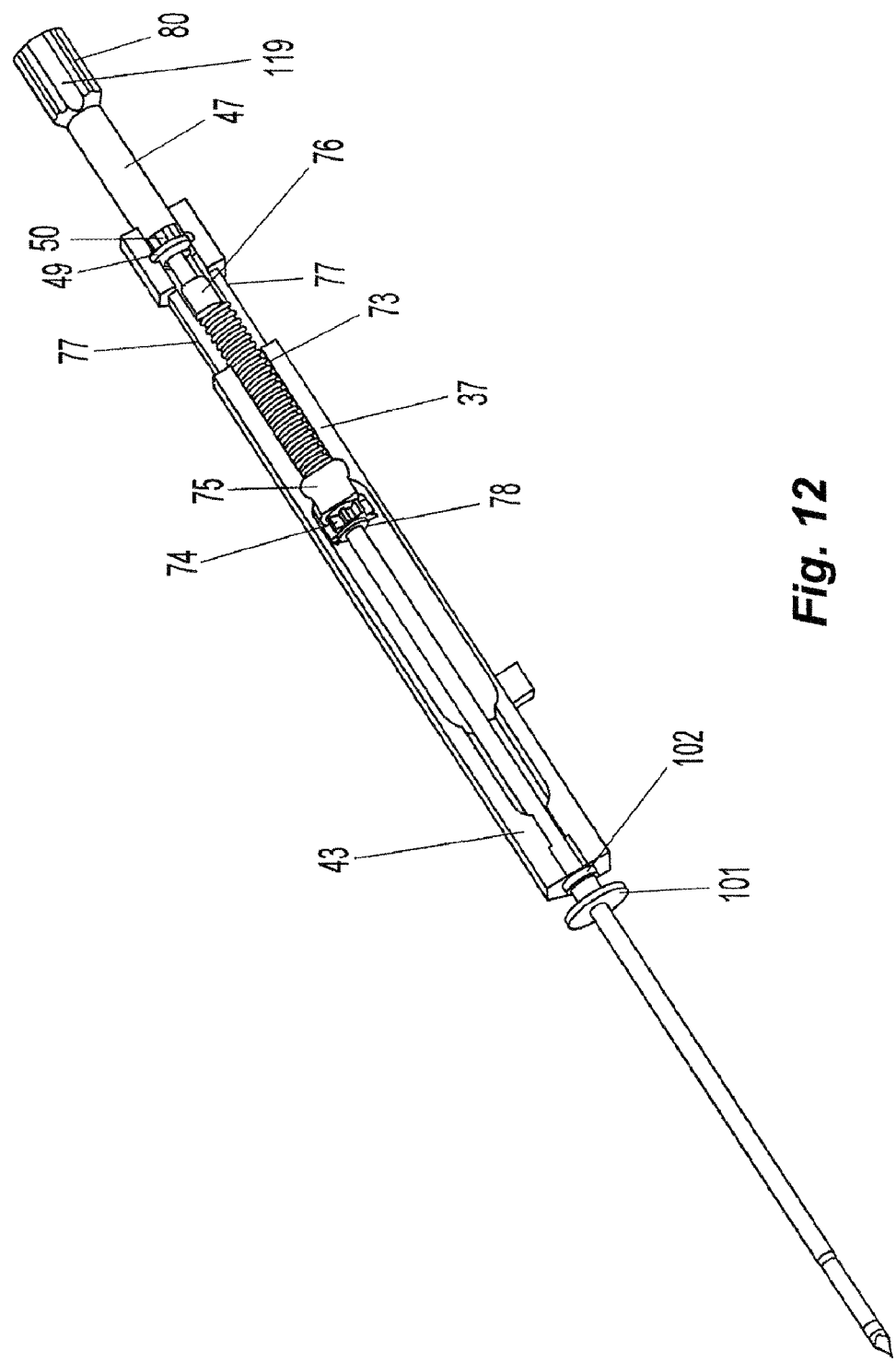
FIG. 12 shows a biopsy needle carrier with press-fitted biopsy needle/cutting sheath and plastic piece (from below, rotated around 90°, perspective view).

The tension slide 28 moves on the threaded bolt and the separating plate 114 and is thus prevented from twisting. One arm 99 of the double-arm lever 33 of the locking device engages with a groove 27 of the tension slide 28 (FIGS. 9a and 10a). The locking device, integrated in the block 26 of the base block 8, consists of the double-arm lever 33, which can swivel about an upright axis 35 (looking in the Y-axis) by means of a compression spring 34. The axis 35, an upright pin, is secured in the boreholes 38 of the base block. In the uncocked condition, the part 99 of the double-arm lever lies in the groove 27 of the tension slide; the compressed spring 34 acts on the part 100 of the lever to press the locking button 88 outward (forward). As soon as the part 99 of the double-arm lever can engage in the recess 82 of the tension slide, the activating button 88 is pressed outward. The tension slide is locked by the locking of the lever part 99 in the cocked condition and can now be triggered when necessary with the activating button 88. Since the tension slide is advisedly made of plastic, it has proven advisable to employ a metal part 83 in the recess, so as not to damage the plastic, since the double-arm lever is made of metal. Unlike the removable element 20, the hand piece 1 with replaced insertion element can be used repeatedly. The cocking distance corresponds to the depth of penetration of the biopsy needle into the tissue. Hence, the length of the lever 99 likewise corresponds to the cocking distance. Since the depth of penetration is generally between 15 and 25 mm, the same hand piece 1 can be used for different depth of penetration by appropriately configuring the length of the lever 99 and changing the setpoints of the control system.

The tension slide 28, which adjoins the block 26, is arranged at equal height and is roughly equal in cross section. On its top side, the tension slide has two brackets 40. The upward pointing surface 41 of the tension slide, as well as the upward pointing surface 44 of the block 26, and the upward pointing surface of the extension 42 of the basic block 8, together form a planar bearing surface for the lower sliding surface 43 of the biopsy needle carrier 37 mounted thereon. The biopsy needle carrier is made of plastic. As the tension slide is moved from the starting uncocked condition (FIG. 9a) to the cocked condition (FIG. 10a), i.e., to the right, the biopsy needle carrier 37 held by the brackets 40 slides across the surface 42 and 44. It is also conceivable that the sliding surfaces are configured not planar, as in the sample embodiment, but instead have specially configured sliding surfaces; the important thing is that the biopsy needle carrier 37 can slide easily and straight on the sliding surface and the biopsy needle can penetrate straight into the tissue, or tumor, after triggering the activation button 88. Therefore, the upper outer contour of the biopsy needle carrier is also configured correspondingly to the inner contour of the housing cover and has only slight play relative to the housing cover in order to prevent the biopsy needle from deviating upward.

Above the U-shaped space 24 for the toothed roller 23, at the height of the sliding surface 42, the basic block 8 has a U-shaped upwardly open holder 36, for inserting the biopsy needle/cutting sheath among other things. This holder serves primarily as a radial thrust bearing, i.e., as a prop for the actuating part connected to the cutting sheath, the gear 74, or the plastic disk 78, in order to bring the tension slide into its cocked position by means of the actuating device 106, as shall be described afterwards. In the upper rear part of the base block there is provided another U-shaped insert element 62, in which the free end 61 of the threaded spindle of the vacuum pressure-generating device 5 is inserted. In the middle, top, of the base block 8 is the recess 45, into which the dog 12 of the locking latch 11 of the housing cover is forced. A cover 46 arranged on the base block 8, pointing to the left, separates the space of the actuating motors and the board from the upper left part of the housing interior, which is used primarily to keep the exchangeable biopsy needle carrier 37, including biopsy needle and cutting sheath. The cover 46 protects the electric gear motors and the board against dirt. The board for the electronics lies between the actuating motors and underneath the middle rib.

FIG. 2 shows the biopsy needle carrier 37, which can be inserted into the brackets 40 of the tension slide 28 with biopsy needle 2 and cutting sheath 3, as well as other parts. The hollow, round circular biopsy needle 2 has a needle tip 70, which adjoins the sample removal chamber 71 (FIGS. 11a-11e). The biopsy needle 2, which is round in cross section, is surrounded by a coaxially arranged cutting sheath 3, round in cross section, having a cutting edge 72 at its left end, facing the sample removal chamber, which serves to cut out the tissue sample after the biopsy needle is introduced (with sample removal chamber closed) and after the sample removal chamber is opened and the sample is sucked into the sample removal chamber. The cutting edge preferably stands perpendicular to the lengthwise axis of biopsy needle and cutting sheath. The cutting process occurs by rotation and simultaneous lengthwise displacement of the cutting sheath by means of the threaded spindle drive. It is also conceivable that the motion occurs not continuously, but stepwise or vibrating, i.e., the feed process moves back and forth with short intervals.

At the other, proximal end of the cutting sheath, away from the cutting edge 72, there is fastened a threaded spindle casing 73 with a gear 74 arranged at the end face of the threaded spindle casing. The threaded spindle casing with gear is arranged on the cutting sheath and prevented from turning and shifting. The threaded spindle cooperates with a threaded spindle nut 75, which is firmly press-fitted in the biopsy needle carrier 37. The gear 74 lies to the left, i.e., before the spindle casing begins. When the threaded spindle casing is turned by means of the gear 74, the cutting sheath is rotated and shifted in lengthwise direction along the biopsy needle 2.

The gear 74 at the left end of the threaded spindle engages with the toothed roller 23 after the biopsy needle carrier is inserted in the brackets 40. So as to allow for inserting the biopsy needle carrier 37 into the brackets of the tension slide when the slide is not cocked (FIG. 2), the biopsy needle carrier has two plane parallel recesses 77. When the sliding surface of the biopsy needle carrier 37 is placed on the surfaces 41, 42 and 44, at the same time the cutting sheath is inserted in the holder 36 of the base block 8. To improve the turning of the spindle drive, especially when the holder 36 is used to support the cocking of the tension slide, a plastic disk 78 can be inserted at the left side of the gear, being provided with a slight cone. When the biopsy needle carrier is correctly inserted, it slides to the right by the sliding surface 43 over the surfaces 42 and 41 when the tension slide is cocked. Since the specimen removal chamber is only closed after inserting the biopsy needle carrier, the gear 74 bears against the holder 36. Now, if the toothed roller 23 is driven further in the same direction, the threaded spindle drive will screw the tension slide to the right along the biopsy needle carrier, until it locks; the biopsy needle will be pulled inward, while the cutting sheath remains in its position. After the locking, the cutting sheath protrudes beyond the tip of the biopsy needle. Therefore, after the locking of the tension slide, the cutting sheath is rotated back to the starting position (opposite direction of rotation); the gear 74 will move from left to right in the toothed roller. After releasing of the tension slide, the biopsy needle/cutting sheath with gear slides back to the left with the biopsy needle carrier. Now, the cutting sheath can again be moved to the right in order to open the sample removal chamber.

The right end of the cutting sheath is connected to the hollow biopsy needle by a seal element 76, able to move in rotation, but air-tight, so that neither air can get in between biopsy needle and the cutting sheath coaxially surrounding it, nor can air escape during excess pressure. On the right end of the biopsy needle 2 is mounted air-tight a round, likewise hollow plastic part 47, being frictionally joined to the biopsy needle. The plastic part 47 has a bearing element 49 at its left end, which is press-fitted into the biopsy needle carrier; at its right end, protruding from the hand piece 1, there is inserted another plastic part 112, which can turn relative to the plastic part 47 and the biopsy needle 2. Between biopsy needle and plastic part 112 there is inserted an O-ring seal. The plastic part has a plug 17 at its right end, onto which the connection element 4 is placed air-tight.

There is also a knurled disk 80 on the right part, protruding from the biopsy needle carrier and the housing, by which, when rotated, the position of the sample removal chamber can be adjusted radially, without altering the position of the cutting sheath. One rotation of the biopsy needle involves only one rotation of the sample removal chamber and, thus, the sample removal device. The plastic part 47 with biopsy needle and cutting sheath is press-fitted into the biopsy needle carrier with the bearing element 49 and the threaded spindle nut 75. The biopsy needle can rotate in the biopsy needle carrier and is mounted in the cutting sheath by the bearing element 49 and its narrow guide in the cutting sheath, and it can shift in the lengthwise axis with the biopsy needle carrier. As described above, the cutting sheath is axially movable by rotation relative to the biopsy needle. To the right of the bearing element 49 a polygon 50 is arranged on the plastic part, which can lock with the biopsy needle carrier by tension, so that the sample removal chamber of the biopsy needle can be brought into the most favorable position for the biopsy removal and held there by means of the knurled disk 80.

Details of the sample removal chamber and the tip of the biopsy needle are represented in FIGS. 11*a*-11*e*. The sample removal chamber 71 adjoining the needle tip 70 is open from above for approximately 25% of its cross section. The cutting edges can be ground or sharpened. The sample removal chamber is between approximately 15 and 25 mm in length. It adjoins the cavity of the biopsy needle. At the transition, i.e., the right end of the sample removal chamber, the cross section of the cavity of the biopsy needle is closed between approximately 50% and 75% by a narrowing, e.g., a stopper 79 (FIGS. 11*b*-11*e*). The height of the stopper is chosen such that it extends downward past the recess of the sample removal chamber. In this way, the vacuum will especially draw in the tissue sample through the continuous opening of the sample removal chamber and bring the tissue sample up against the wall of the sample removal chamber.

When there is excess pressure in the cavity of the biopsy needle, the narrowing or stopper has a pressure boosting effect. The stopper has roughly the length of 10 mm and is glued or welded into the cavity. When using laser welding, it has proven to be advantageous to make the left side of the stopper thin for a short length, around 2 mm, by removing material at the end surface. As a result, in this region at the end surface the tube of the biopsy needle is welded to the end surface of the stopper and is air-tight at the end surface. The stopper can also be of shorter length, as long as the same effect is achieved. Thus, the stopper can also be replaced by a lip or dog of approximately the same height. The important thing is that the narrowing is configured such that the vacuum is brought to bear primarily from the bottom in the sample removal chamber, so that the sample clings to the wall of the sample removal chamber during the cutting process and does not change in length. It has also proven to be advantageous to provide additional fixation means on the sample removal wall.

The suctioning of the sample from the bottom into the sample removal chamber produces, first, a high fill ratio of the sample removal chamber and, second, especially thanks to its configuration, a good fixation of the sample on the wall. Since the cutting sheath separates the sample at the outside of the biopsy needle, this firm suctioning of the sample into the interior is also preserved during the separation process. Furthermore, thanks to the cutting sheath arranged on the outside, thanks to the vacuum applied, no tissue is suctioned into the hollow cutting sheath and thus the tissue cannot get twisted or turned by the rotating lengthwise movement of the cutting sheath, as it is held fast in the interior of the cutting sheath. This improves the quality of the sample, since the pathologist obtains original material corresponding to the cross section of the cut and not being twisted or deformed. When the sample is ejected under pressure, a complete cleaning of the sample removal chamber occurs in addition through the stopper 79, so that no comingling occurs when used repeatedly. Since the vacuum generating device is used at the same time as a pressure generating device, the entire cavity is cleaned, especially that of the needle.

Figure 13:
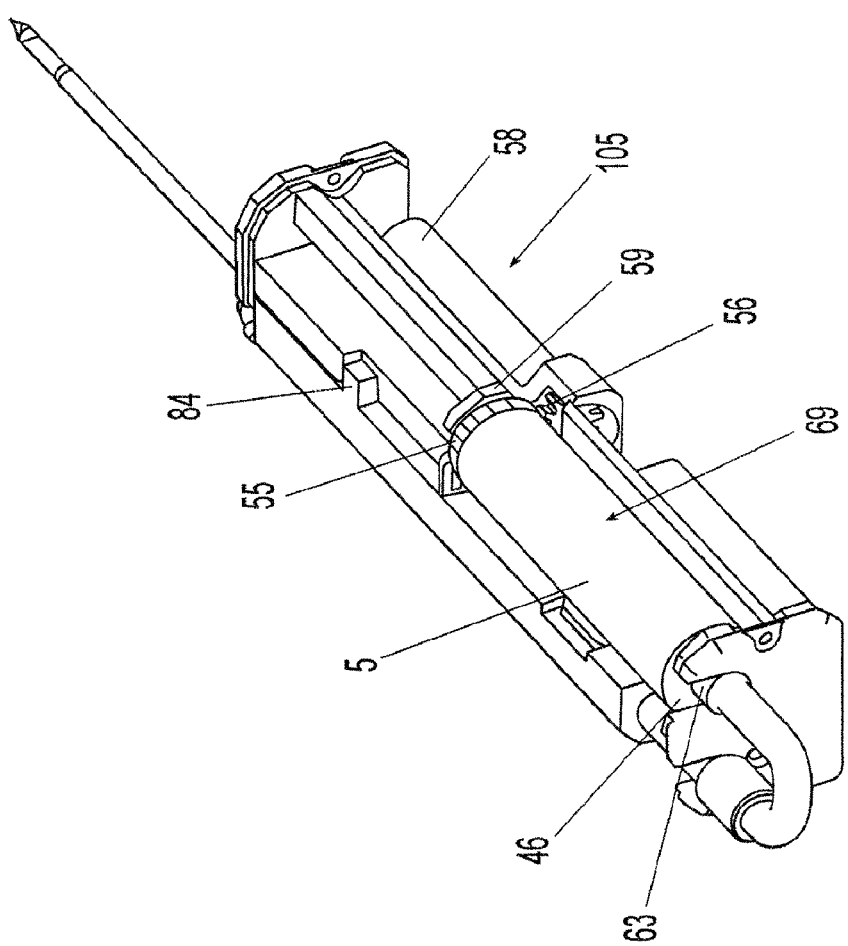
FIG. 13 shows a vacuum/pressure device, installation and actuation (seen from rear, perspective view).

FIG. 13 shows the drive and the installation of the vacuum pressure-generating device 5 (view from the rear, i.e., opposite the Z-axis, housing cover and lower housing piece left out). In the upper, rear, right region, the vacuum pressure-generating device 5 is arranged as a piston/cylinder unit 69. It consists of a syringe body 52 with threaded spindle 53 arranged inside, at whose end facing the syringe bottom 51 there is fastened a plunger 54 with seal elements—as is commonly known with syringes (FIGS. 14*a*-14*d*). At the end of the syringe body 52 facing the base block 8, a threaded spindle nut 48 is arranged on the threaded spindle with a gear 55 formed at the circumference. The threaded spindle nut has one or more thread turns. The threaded spindle 53 interacts with the threaded spindle nut 48. The spindle has a pitch of around 5 mm per turn, so that at each rotation the plunger is moved out from the syringe body by a precisely defined amount, i.e., away from the syringe bottom 51, or toward the syringe bottom, depending on the direction of turning.

The toothed crown 55 arranged on the circumference of the threaded spindle nut meshes with the drive pinion 56, which is fastened on the take-off shaft of the DC gear motor 58. The take-off shaft of the DC gear motor 58 is mounted in the base block 8; for this, the take-off shaft is inserted into the transverse plate 59 of the base block. When the DC gear motor 58 is activated, the plunger is moved toward the syringe bottom or in the direction of the base block 8, depending on the direction of turning. The drive motor used is likewise a DC motor with high speed, connected to a planet transmission with high reduction ratio. It corresponds to the motor already described for the cocking mechanism.

Figure 14:
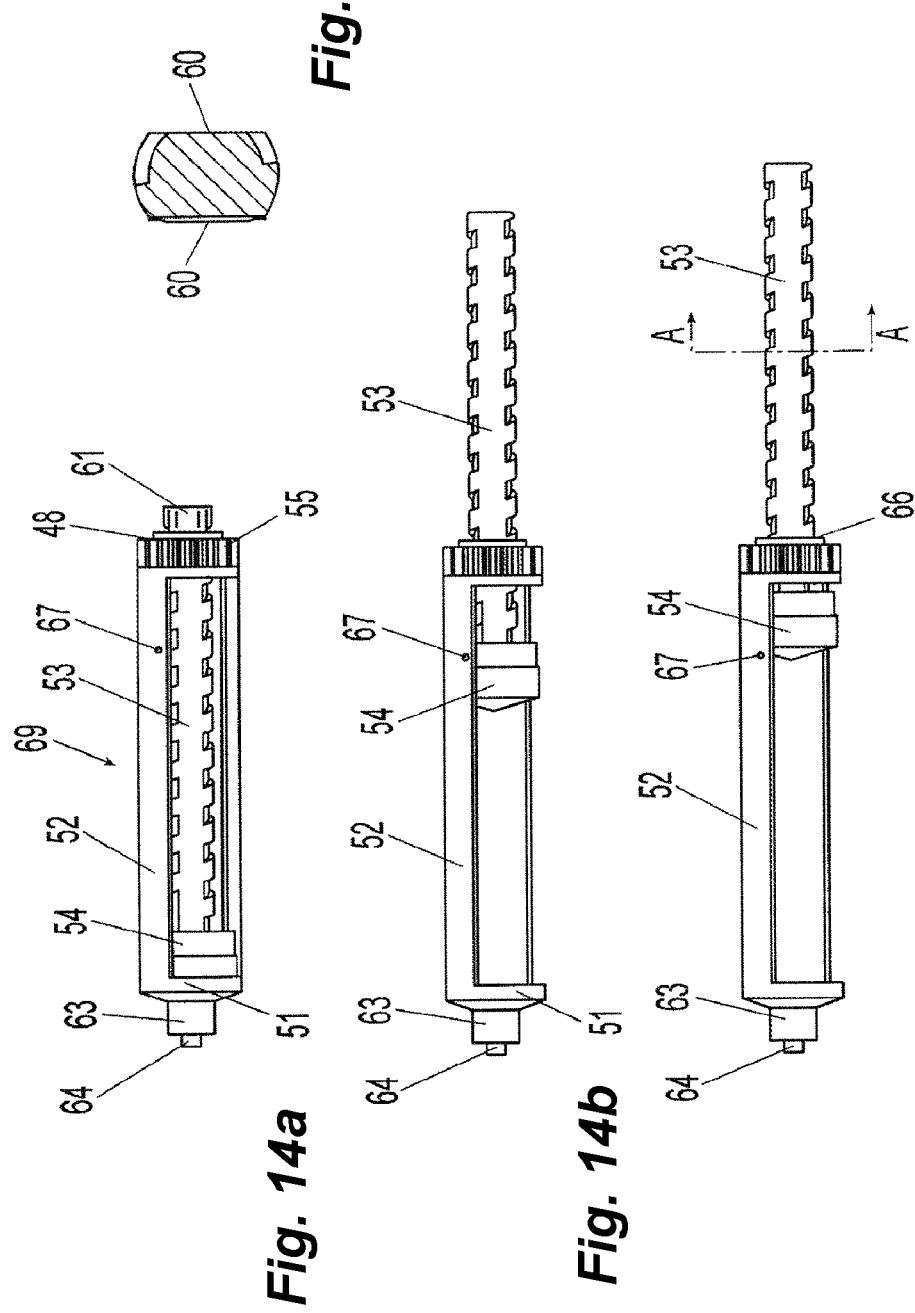
FIG. 14a shows a vacuum/pressure device with plunger mounted on the bottom of the syringe (starting position for creating a vacuum and end position for generating pressure, partially cut away).
FIG. 14b shows a vacuum/pressure device with retracted plunger; end position of the vacuum stroke (partially cut away).
FIG. 14c shows a clearing of the ventilation opening (syringe plunger retracted beyond ventilation opening; pressure equalization position, partially cut away).
FIG. 14d shows a cross section A-A through the threaded spindle in FIG. 14c.

The plunger 54 is configured in familiar fashion as a syringe plunger. The syringe body made from plastic, being a cylinder with a bottom, is transparent. In order to prevent a twisting of the threaded spindle 53 upon actuation of the threaded spindle nut, the two opposite surfaces 60 of the threaded spindle are planer in configuration (FIG. 14*d*). The threaded spindle is inserted into the insert element by its free end. The spacing between the surfaces of the threaded spindle corresponds to the width of the U-shaped insert element 62 of the base block 8. There is only slight play between the U-shaped cross section of the insert element and the spindle surfaces at either end. The threaded spindle nut thrusts against the base block. In order to prevent the syringe body 52 from sliding out upon turning of the threaded spindle nut, the bearing surface at the base block 8 is slightly conical toward the bottom. The connection piece 63 of the syringe body 52 is inserted into the passage 16 of the right end cover 7 so that the syringe body is held in roughly horizontal position.

In order to make the threaded spindle easy to turn, the threaded spindle nut with toothed crown has a chamfer 66 around 1.5 mm in thickness at the side facing the base block. Since, furthermore, the surface of the rib 59 on the base block 8, which interacts with the chamfer 66 of the threaded spindle nut 48, is inclined from top to bottom, the vacuum pressure-generating device is pulled downward during operation. To create a sufficient vacuum of around 200 hph in the sample removal chamber, for example, when using a biopsy needle with length of around 250 mm and an internal diameter of the hollow biopsy needle of around 5 mm, one uses a syringe body for 20 ml with a length of around 90 mm. In order to be able to use the syringe body also as a pressure generator, a ventilation opening 67 of around 1.5 mm diameter, for example, is provided after around ¾ of its length, corresponding to the stroke for producing the vacuum (position per FIG. 11*b*).

If the syringe plunger is moved beyond the ventilation opening 67 (FIG. 14*c*)—when the vacuum is no longer required—intake of air (atmospheric pressure) through the ventilation opening 67 will dissipate the previously established vacuum in the hollow biopsy needle. If, then, the direction of turning of the gear motor is reversed, the vacuum pressure-generating device will build up an excess pressure in the system by retraction of the plunger (toward the bottom of the syringe), which brings about the ejection of the tissue sample after opening the sample removal chamber. Moreover, the pressurized air will clean not only the sample removal chamber, but also in particular the inside of the biopsy needle. The stopper narrowing the cavity of the needle will make it difficult or entirely prevent tissue parts from getting into the cavity of the biopsy needle. The narrowing of the needle cavity by the stopper 79 will increase the pressure at the sample removal chamber and thereby improve the ejection of the sample, even when the sample removal chamber is half open.

The handling of the biopsy mechanism shall now be explained more fully. The removable insert element 20, comprising a vacuum pressure-generating device, elastic connection element, biopsy needle carrier with needle and cutting sheath and additional elements connected to it, also contains a guide roller 81 mounted on the needle. This unit, including an insert aid, comes in a sterile package. The plunger 54 in the syringe body 52 comes slightly (1-2 mm) lifted up from the syringe bottom, the sample removal chamber 71 of the biopsy needle 2 is open so that one can make a visual inspection of the chamber prior to inserting. After opening the housing cover 10, the carrier element 37, including biopsy needle 2, cutting mechanism 3, and other parts connected with it, such as the vacuum pressure-generating device 5 hooked up to the connection element 4, is inserted into the connection element provided for this (FIG. 2).

During the insertion process, one must make sure that the gear 74 engages with the teeth of the toothed roller 23; the cutting sheath is inserted from above into the U-shaped holder 36, and at the same time the brackets 40 of the tension slide are introduced into the recesses 77 of the carrier element; the guide roller 81 is inserted in the passage 13, so that the flanks 101 and 102 embrace the left end cover 6. The cutting sheath is mounted in the guide roller, able to move lengthwise and turn freely; the guide roller itself, however, can no longer move relative to the cutting sheath after being inserted in the left end cover 6. The vacuum pressure-generating device is then inserted at one end into the upward-open insert element 62 of the base block 8 by its free end 61 and at the other end into the U-shaped, upward-open passage 16 by the connection piece 63. The connection piece 63 lies above the switch pin 19.

Since the insert element at the base block has a clear width which just allows the inserting of the threaded spindle provided with surfaces 60 at either end, the threaded spindle is held in the insert element, secure from turning. The toothed crown 55 of the threaded spindle nut 48 engages with the take-off pinion 56 of the gear motor after being inserted. The spacing between the base block at one end and the housing end cover 7 at the other is maintained so that syringe body 52 with the threaded spindle nut 48 placed on the syringe body has just enough room. The unit formed by the syringe body and the mounted gear is held in this way so that it cannot shift axially. After being inserted, the vacuum pressure-generating device lies parallel to the biopsy needle carrier; the connection element describes an arc of around 180°. It should further be noted that the inserting is done when the tension slide is not cocked; this means that the gear 74 engages at the right end of the toothed roller with the sample removal chamber open (FIG. 3). After being properly inserted, the housing cover can be closed. To facilitate the inserting process, an insert aid can be used.

When the housing cover is closed, the connection piece 63 is forced downward and activates the miniature switch by the switch pin 19 built into the end cover of the housing. This activates the electrical system, which is indicated by blinking of the reset diode 91 on the front side of the hand piece 1. The reset diode at first blinks green, which means that the positioning of the individual elements, i e., the inserting process, is not yet finished; the DC gear motor 21 must first close the sample removal chamber 71 with the cutting sheath 3 (the sample removal chamber was partly opened during the inserting). This occurs by twisting the threaded casing connected to the cutting sheath. The cutting sheath moves to the left until the gear 74 comes to bear against the inside of the holder 36. After closing the sample removal chamber, the plastic disk 78 bears against the holder 36 (inside). During this process, or before or after it, the DC gear motor 58 brings the syringe plunger 54 to bear against the syringe bottom 51.

After the starting positions are reached for the vacuum pressure-generating device and the biopsy needle/cutting sheath, the cocking diode 94 and the sample removal diode 92 light up green, and the reset diode goes out. The operator must now decide whether to initiate the cocking of the tension slide or to remove an additional sample, e.g., because he has already previously removed one tissue sample. If the operator presses the cocking button 90, the cocking of the tension slide is initiated; the cocking diode blinks green, the sample removal diode 92 goes out. By pressing the cocking button, the electrical DC gear motor 21 receives current and the DC gear motor actuates the toothed roller 23. The gear 74 meshing with the toothed roller 23 turns the spindle shaft and at the same time the cutting sheath 3 connected to it. Since the spindle nut 75 is press-fitted in the biopsy needle carrier 37 and the gear 74 is supported by the plastic disk 78 against the holder 36, which is firmly connected to the housing by the base block 8, the turning of the threaded spindle casing 73 has the effect of moving the biopsy needle carrier to the right.

At the same time, the biopsy needle 2 connected to the biopsy needle carrier by the bearing element 49 is carried along, resulting in the tip of the biopsy needle moving into the cutting sheath. The biopsy needle carrier 37 is moved to the right by the recess/bracket connection of the tension slide against the action of the spiral spring 31 until the lever 33 of the locking element is forced into the recess 82 of the tension slide by the spring 34. The tension slide is locked in this position. The gear motor receives the control command that the locking position has been reached, e.g., via a photocell installed in the sliding surface of the cover plate, which interacts with the retracted biopsy needle carrier; the direction of turning of the motor is reversed and the cutting sheath is turned back to the right by the amount that the cutting sheath had moved beyond the tip of the biopsy needle by the movement of the tension slide and the biopsy needle.

At the end of this step, the cutting sheath completely closes the sample removal chamber (FIG. 11d), as at the start of the cocking process. The locking diode 95 lights up green; the blinking of the cocking diode 94 goes out. So as to reduce the friction between gear and support element during the cocking process, the plastic disk 78 is arranged between gear 74 and holder 36. Now, the biopsy needle of the biopsy mechanism is inserted, for example, in a previously mounted coaxial cannula. The proximal end of the mounted coaxial cannula receives a seal, designed so that it seals off the space between cutting sheath and cannula, on the one hand, and allows an easy insertion of the biopsy needle with cutting sheath, on the other. The seal ring prevents air from the outside getting sucked in through the space between cannula and cutting sheath. The seal ring likewise prevents fluid (cytological material) from escaping after the biopsy needle is introduced or inserted. Thus, the possibility of the disinfected hand piece 1 getting dirty is nearly precluded; on the other hand, the flank 101 of the sterile guide roller 81 prevents the sterile cannula from getting dirty by reason of the hand piece 1. The tip of the biopsy needle is brought up in the cannula to the tumor and, after being correctly positioned, thrust into the tumor.

The shot is triggered by pressing the activation button 88. This has the result of swiveling the double-arm lever 33 about the axis 35 to release the tension slide. The tension slide is hurled to the left by spring action. The sample removal diode lights up green, the cocking diode goes out. By operating the program button 89, the sample removal sequence is enabled; the sample removal diode 92 blinks green. At first, the DC gear motor 58 will activate the vacuum pressure-generating device. The plunger of the vacuum pressure-generating device is moved in the direction of the base block, i.e., away from the bottom of the syringe, until it reaches a position just before clearing the ventilation borehole 67 (FIG. 14b). The vacuum is generated in the system. After reaching its end position, the system activates the motor 21, the cutting sheath which closes the sample removal chamber is opened via the gear/spindle drive. During the opening process, the partial vacuum prevailing in the system sucks in the tissue and any cytological fluid (cytological material) into the sample removal chamber. Cytological fluid will also flow thanks to the vacuum into the biopsy needle cavity and the vacuum pressure-generating device.

It has proven to be advantageous to direct the partial vacuum by the stopper 79 primarily at the lower region, the lower side, of the sample removal chamber, and the stopper 79 will prevent or impede tissue from getting into the biopsy hollow needle. When the sample removal chamber is fully open—the tissue sample is accommodated in the sample removal chamber—the gear motor 21 is reversed and the sample removal chamber is closed. By turning the cutting sheath, the tissue is separated by the cutting edge 72 of the sheath 3 during the closing process. In order to reliably cut through the tissue filaments, it is advantageous to move the cutting sheath 3 beyond the distal end of the sample removal chamber (around 2 mm). In order to accomplish this, it is only necessary to program accordingly the microprocessor where the control data is kept. Because of the special configuration of the sample removal chamber and thanks to the vacuum applied, the tissue sample is held in the chamber without torsion, so that the tissue sample is not twisted or turned by the rotating and lengthwise moveable cutting sheath 3 which surrounds the biopsy needle on the outside, as described.

After the sample removal chamber is closed, the DC gear motor is activated for the vacuum generating unit 5. The plunger 54 is first retracted far enough to clear the ventilation opening (FIG. 14c). After the vacuum is dissipated in the system, the plunger travels toward the vacuum bottom until the ventilation borehole is again closed, in order to prevent the outflow of bodily fluid (cytological fluid). The blinking of the sample removal diode 92 goes out. The ejection diode 93 lights up green. The biopsy needle with closed sample chamber is extracted from the cannula. After the removal of the biopsy unit and providing a vessel to receive the tissue sample and fluid, the program button 89 is again operated and the ejection diode 93 starts to blink. At first, the gear motor 21 of the cutting sheath is operated to open the sample removal chamber roughly halfway. After this, the DC gear motor 58 of the vacuum pressure-generating device is activated. The turning direction of the DC gear motor 58 remains and the threaded spindle 53 with plunger moves in the direction of the syringe bottom, so that now an excess pressure is created in the system. The plunger travels up to the plunger bottom, and the actuating motor 58 is deactivated.

The gear motor 21 moves the cutting sheath back across the sample removal chamber after the plunger has reached the plunger bottom. Thanks to the excess pressure built up in the system, the sample is forced out under pressure into a waiting laboratory vessel even when the sample removal chamber is halfway open, and at the same time the cavity of the vacuum pressure-generating device, the biopsy needle and the sample removal chamber is cleared of tissue particles and fluid. The ejection of the sample when the sample removal chamber is around halfway open is so that the ejection of the tissue sample is assured and the tissue sample does not fall back into the chamber as a result of premature dissipation of the excess pressure. The narrowing of the cavity of the biopsy needle by the stopper 79, which prevents or impedes tissue from getting into the cavity of the biopsy needle, proves to be especially advantageous when removing the sample, since the narrower cross section boosts the ejection pressure. The best ejection results were therefore achieved with the sample removal chamber halfway open; i.e., the cutting sheath clears half of the sample removal chamber. The excess pressure also forces tissue fluid out of the sample removal chamber and cleans it.

After the sample removal chamber is fully open, the removal and cleaning is finished, and the ejection diode goes out. The reset diode 91 lights up green. If no further samples are to be removed now, the housing cover is opened and the removable element 20 is taken out. When the housing cover 10 is opened, the system is deactivated by the miniature switch 18. However, if an additional sample is to be taken from the same tissue environment, the operator presses the program button 89 and the reset diode 91 starts to blink. The vacuum pressure-generating device, as well as the cutting sheath, are again adjusted as described. At the end of the process, the reset diode 91 goes out and the sample removal diode lights up. The next steps of the process occur in the sequence already described. The process can be repeated as often as desired. At the end, the operator need only decide whether to take another sample or to conclude the sampling and open the housing cover.

As already described, in order to enhance the operating safety, a delay circuit can be provided for individual steps such as "cocking" and "ejection of sample". Furthermore, the light-emitting diodes can have different colors, so that one can distinguish between work in the tissue and that outside the tissue. If it is required to take the sample from a location of the tumor that does not lie directly above or at the sample removal chamber after being inserted, i.e., it lies to the side, the position of the sample removal chamber 71 can be turned by means of the knurled disk 80. So that the operator can recognize this radial positioning of the sample removal chamber, a marking in the form of a notch 119 is made on the knurled disk, pointing upward when the opening of the sample removal chamber points upward. The biopsy needle is fixed in the particular position by the surfaces of the polygon 50 and the elastic forces in the carrier piece. The sampling process is the same as already described.

After completion of the biopsy, the interchangeable element 20 (vacuum/pressure device, biopsy needle/cutting device with all elements arranged on it) is removed from the top after releasing the cover. To make it impossible to open the housing when the tension slide is cocked, a safety tab 84 is arranged on the biopsy needle carrier, which bears against the left end surface 85 of the closure mechanism in the cocked condition. In this way, the closure mechanism, moveable in the X-axis, can no longer be moved to the left into the open position and thus the dog 12 can no longer be taken out from the recess 45. On the other hand, the housing cover also cannot be closed if the carrier unit has been inserted in the cocked condition, since the safety tab prevents the latch from being introduced into its designated space. The surface 85 of the latch adjoins the safety tab. The battery charge diode 96 is turned off as soon as the housing cover is opened. When the cover is closed and the insert element 20 is installed, the battery charge diode indicates whether sufficient energy is available.

Basically, it is conceivable to control all steps individually by hand for the removal of a sample, as well as the cocking of the slide, etc., by activating and deactivating the two gear motors. However, it is expedient to group together the individual steps of the sequence and have them run automatically, with only the following step initiated by activating a switch. This semiautomatic method, as described above, has proven to be especially advantageous.

Figure 15:
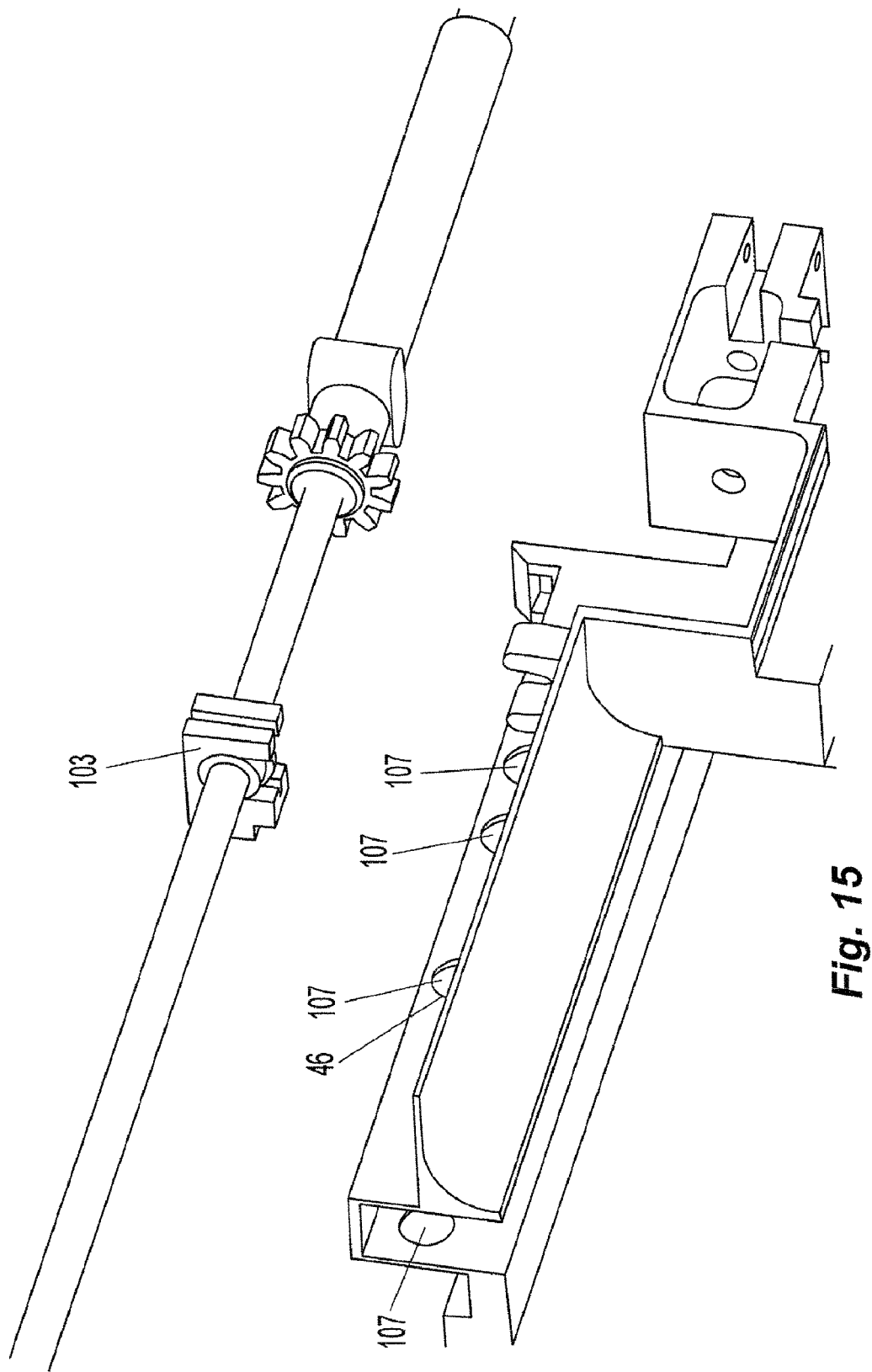
FIG. 15 shows a base block and biopsy needle/cutting sheath, prepared for fitting out with photocells and miniature switches to detect actual values.

Basically, there are two conceivable methods for detecting the actual values and comparing them to the nominal values. One method is based on measuring the lengthwise displacement of the threaded spindle as it is pulled out or pushed in, and measuring the axial displacement of the cutting sheath or the biopsy needle carrier. In order to detect these changes, photocells or miniature switches are arranged inside the housing, in particular on the extension of the base block 8. In addition, a positioning finger 103 is mounted on the cutting sheath, while the free end 61 protruding from the plunger unit can be used as a measuring point for the threaded spindle of the vacuum pressure-generating device; if the front edge of the biopsy needle carrier is used as a measuring point with a photocell, no additional positioning finger is required. The embedded photocells are covered with suitable transparent material in case of possible contamination. The positioning finger 103 engages with a slot in the biopsy needle holder. At appropriate places on the extension of the base block 8 there are provided recesses 107, in which photocells or miniature switches are installed, which interact either with the free end 61 of the plunger spindle, the positioning finger 103, or an edge of the biopsy needle carrier (see FIG. 15). These signals (actual value) are processed in the electronics to form the control signals.

The other system is based on measuring the number of revolutions of the DC motors. In this case, a pickup is mounted on the shaft of the DC motor, which interacts with a photocell mounted on the housing of the DC motor. In this way, the number of revolutions of the motor is measured. Since the DC motors operate with a speed of around 10,000 to 12,000 rpm, depending on the load, and on the other hand the secondary planet transmission arranged at the take-off end which interacts with the spindle drive considerably reduces the number of revolutions, an exact lengthwise control is possible. The lengthwise displacement by the spindle drive is a constant value proportional to the operating speed and is therefore sufficient as a control signal for the lengthwise displacement. In order to precisely determine the position of the cutting sheath 3 as well as the plunger 54 at the start, i.e., after inserting the removable element and closing the housing cover 10, the DC gear motor 58 rotates the plunger 54 until it strikes against the syringe bottom and the DC gear motor 21 brings the drive of the cutting sheath to a zero position by moving the gear 74 until it strikes against the threaded spindle nut 75. (The threaded spindle nut 75 abuts against the gear 74.) From this zero position, the individual steps are then controlled by comparing the settings and the actual values. The necessary cables from the measuring pickup to the electronics are accommodated in the housing, as is the board with the electronic components. A microprocessor arranged inside the housing, under the cover, with the setpoint values stored in it, controls the individual processes.

Figure 16:
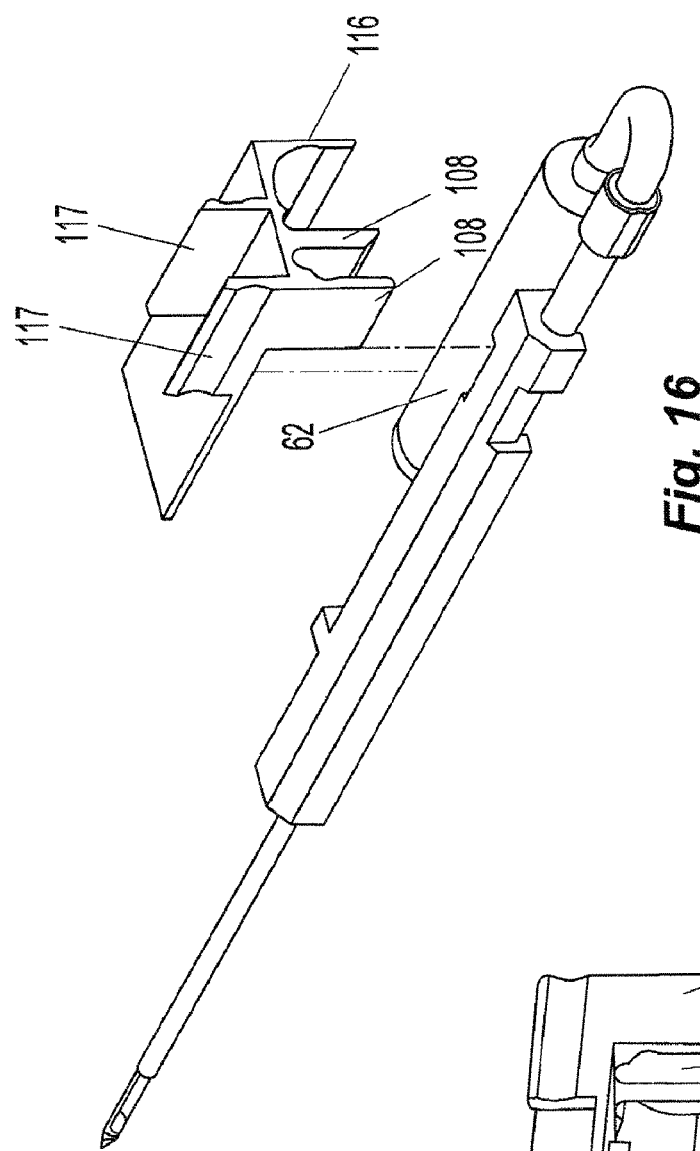
FIG. 16 shows an insert element lifted off from the insert aid (perspective view).
Figure 17:
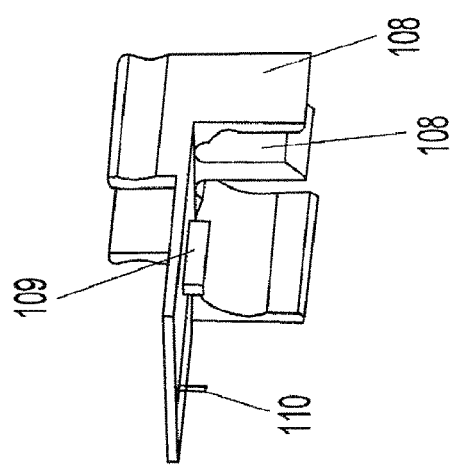
FIG. 17 shows an insert aid (perspective view).

In order to enable easy insertion of the removable insert unit, the insert aid shown in FIGS. 16 and 17 can be used. As FIGS. 16 and 17 show in particular, the biopsy needle carrier is enclosed by two brackets 108 and axially fixed in the holder by an additional cross piece 109, so that it comes to lie parallel to the vacuum/pressure device in the insert aid. The vacuum pressure-generating device is likewise enclosed by the bracket 116 at one side and by the centrally arranged bracket 108 on the other side. In addition, a pin 110 engages with the ventilation borehole 67. This ensures that the vacuum pressure-generating device is oriented parallel to the biopsy needle carrier (FIG. 1). The parts so oriented are fixed in the insert aid so that they can easily be inserted from above into the hand piece 1 by means of the holder piece 117. Since the parts come in a sterile package with the insert aid, the interchangeable element 20 can be removed from the package without manual contact and be inserted in a sterile manner into the hand piece 1. The brackets are slightly slanted for easier lodging of the vacuum pressure-generating device and the biopsy needle carrier. Since the insert aid is made of plastic, the installed parts can easily be held in place by clamping, thanks to appropriate choice of the tolerance and flexibility.

The tip of the needle unit of the biopsy device can be placed directly on the tissue being sampled and inserted into the tissue. It can be expedient, however, to first position a coaxial cannula and then introduce the portion of the needle unit (consisting of biopsy needle and cutting sheath) protruding from the hand piece 1 of the biopsy device into the coaxial cannula 125. In this case, one should make sure that, when the vacuum is created for sucking in the tissue sample, no air can get in from the outside into the space between the inner surface of the coaxial cannula and the outer surface of the needle unit. In the coaxial cannula (FIG. 18) consisting of a tube 121 with cap 122 placed at the proximal end, the tube 121 at the proximal end has a seal element 123 (e.g., a properly dimensioned silicone hose), into which the needle unit is placed. In order to insert the coaxial cannula, a spike 124 is connected to the coaxial cannula 125. The spike 124 has a tip 126 protruding beyond the distal end of the coaxial cannula in the inserting state. The connection between coaxial cannula and spike is a screw fastening, for example, so that the spike cap is configured as a screw cap 127. The screw cap is screwed onto the proximal end of the cap 122. The tube of the coaxial cannula is held in the cap 122 by clamping, for example. After inserting the coaxial cannula, the spike is removed and the needle unit of the biopsy device (in the cocked condition) is introduced and positioned in the coaxial cannula (FIG. 20). The distal flank 101 of the guide roller is placed on the proximal end surface 128 of the cap. After the tension slide is released, the needle tip with the sample removal chamber is forced into the tissue to its full length.

The depth of penetration of the biopsy needle unit of the biopsy device is between 20 and 35 mm, depending on the selected size of needle. In general, it is 20 mm. In the case of small breasts or tumors lying just below the skin, the depth of penetration of the biopsy needle is therefore too deep, since the biopsy device is placed directly or by means of the guide roller onto the coaxial cannula and the depth of penetration cannot be changed at the device. The depth of penetration is device-fixed. In order to be able to use the same biopsy device with the same biopsy needle and same depth of insertion and the same, i.e., uniform coaxial cannula with same overall length and less depth of insertion, one or more spacing pieces 129 are placed medially onto the biopsy needle prior to insertion; thus, these lie medially in front of the guide roller mounted in the housing and the proximal end surface 128 of the cap 122. Thus, by introducing spacing pieces or a spacing piece, the depth of penetration can be changed for the same depth of insertion provided in the device.

After inserting the spacing piece, the tip of the biopsy needle in the cocked condition no longer projects slightly from the coaxial cannula, as when no spacing piece is used, but rather lies in the coaxial cannula. The depth of penetration is thus reduced by the length L of the spacing piece (also see FIGS. 20 and 21). This does not impair the functioning of the sample removal chamber or the operation of the cutting sheath. For example, if a spacing piece of 10 mm is used with a depth of needle penetration of 20 mm, the depth of penetration will be reduced to 10 mm. Of course, the spacing piece can be made up of one or more parts, i.e., when using spacing pieces of 5 mm thickness, two spacing pieces are necessary to reduce the depth of penetration by 10 mm. The adding of spacing pieces or one spacing piece of corresponding length offers the possibility of using a uniform coaxial cannula including a uniformly added insertion spike 124 for various depths of penetration. The same result regarding a reduced depth of penetration could also be achieved by using caps of different height or by mounting the spacing pieces on the cap, which is equivalent to the threaded-on spacing pieces.

LIST OF PARTS 1 hand piece
2 biopsy needle
3 cutting sheath
4 connection element
5 vacuum pressure-generating device
6 housing end cover (left)
7 housing end cover (right)
8 base block
9 housing lower piece
10 housing cover
11 locking latch
12 dog
13 passage
14 borehole
15 passage
16 passage
17 plug
18 miniature switch
19 switch pin
20 removable element
21 DC gear motor
22 wall
23 toothed roller
24 U-shaped space
25 wall
26 block
27 groove
28 tension slide
29 threaded borehole
30 bolt
31 spiral spring
32 end piece
33 double lever
34 pressure spring
35 axis
36 holder
37 biopsy needle carrier
38 boreholes
40 brackets
41 surface of tension slide
42 extension of surface
43 lower sliding surface
44 surface of block 26
45 recess
46 cover
47 plastic part
48 threaded spindle nut
49 bearing element
50 polygon
51 syringe bottom
52 syringe spindle
53 threaded spindle
54 plunger
55 gear (toothed crown)
56 drive pinion
57 board
58 DC gear motor
59 transverse plate
60 surfaces
61 free end
62 insert element
63 connector
64 outflow connector
65 recess
66 chamfer
67 ventilation borehole
69 piston/cylinder unit
70 needle tip
71 sample removal chamber
72 cutting edge
73 threaded spindle casing
74 gear
75 threaded spindle nut
76 seal element
77 recesses
78 plastic disk 79 stopper
80 knurled disk
81 guide roller
82 recess
83 metal part
84 safety tab
85 end surface
87 center rib
88 activating button
89 program button
90 cocking button
91 reset diode
92 sample removal diode
93 ejection diode
94 cocking diode
95 locking diode
96 battery charge diode
97 passage
98 passage
99 arm of the double-arm lever
100 part of the lever
101 flanks of the guide roller left
102 flanks of the guide roller right
103 position finger
104 axis
105 actuating device (vacuum)
106 actuating device (biopsy needle, cocking mechanism)
107 recesses
108 brackets
109 cross piece
110 pin
111 storage battery
112 plastic part
113 surface
114 separating plate
115 guide borehole
116 fastening
117 holding pieces
119 notch
120 edge of needle carrier
121 tube
122 cap
123 seal element
124 spike
125 coaxial cannula
126 tip
127 screw cap
128 end surface
129 spacing piece
L=length of spacing piece

What is claimed is:

1. A biopsy device, comprising: a housing containing an electric power source and a tension slide, wherein the tension slide is configured to be moved to a cocked position against an action of a first spring; a releasable locking mechanism configured to lock the tension slide in the cocked position; and a removable element configured for insertion into the housing, the removable element having a cutting sheath configured to couple the electric power source to the tension slide, the electric power source configured to rotate the cutting sheath to move the tension slide to the cocked position.

2. The biopsy device of claim 1, further comprising a control panel attached to the housing, the control panel having a first control device configured to control the electric power source to rotate the cutting sheath to position the tension slide in the cocked position, and the control panel having a second control device configured to release the releasable locking mechanism when the tension slide is in the cocked position such that the tension slide is moved by the first spring away from the cocked position.

3. The biopsy device of claim 1, the removable element having a biopsy needle coaxial with the cutting sheath, and comprising a spacing piece positioned onto the biopsy needle and the cutting sheath to set a depth of penetration of the biopsy needle and the cutting sheath, wherein the depth of penetration is reduced by increasing a length of the spacing piece.

4. The biopsy device of claim 1, wherein the removable element includes a carrier configured to rotatably mount the cutting sheath, and wherein when the cutting sheath is rotated the cutting sheath is moved both longitudinally and rotationally relative to the carrier.

5. The biopsy device of claim 1, wherein the removable element includes a carrier, a biopsy needle, and the cutting sheath, the biopsy needle having a sample removal chamber, the carrier configured to mount the biopsy needle and the cutting sheath, the cutting sheath being rotatable relative to the carrier to effect a longitudinal movement of the cutting sheath along the longitudinal axis relative to the biopsy needle in a proximal direction to open the sample removal chamber of the biopsy needle, and the cutting sheath being rotatable relative to the carrier to effect a longitudinal movement of the cutting sheath along the longitudinal axis relative to the biopsy needle in a distal direction to close the sample removal chamber of the biopsy needle.

6. The biopsy device of claim 5, the removable element including a pump having an elongate cylinder and a plunger, the pump being coupled in fluid communication with the sample removal chamber.

7. The biopsy device of claim 5, the removable element including a pump to build up pressure at the sample removal chamber when the sample removal chamber is closed.

8. The biopsy device of claim 7, the electric power source configured to move the cutting sheath in the proximal direction across the sample removal chamber to release the pressure from the sample removal chamber.

9. The biopsy device of claim 1, the removable element including a pump and a sample removal chamber, the pump having an elongate cylinder and a plunger, the pump being coupled in fluid communication with the sample removal chamber, the pump configured such that moving the plunger inside the elongate cylinder in a first direction generates a vacuum at the sample removal chamber and moving the plunger inside the elongate cylinder in a second direction opposite the first direction builds pressure at the sample removal chamber.

10. The biopsy device of claim 1, the removable element having a biopsy needle and a knob, the biopsy needle having a sample removal chamber, the knob being coupled to the biopsy needle, wherein a manual rotation of the knob results in a positioning of the sample removal chamber at a selected rotational position.

11. The biopsy device of claim 1, wherein the removable element includes a biopsy needle coaxial with the cutting sheath, and the removable element includes a carrier for mounting the biopsy needle and the cutting sheath, the removable element including a plastic part having a polygonal portion that is mounted to a proximal end of the biopsy needle, wherein an interaction between the polygonal portion and the carrier during a rotation of the biopsy needle intermittently resists rotation of the biopsy needle.

12. A biopsy device, comprising: a housing containing an electric power source and a tension slide, wherein the tension slide is configured to be moved to a cocked position against an action of a first spring; a releasable locking mechanism configured to lock the tension slide in the cocked position; a removable element configured for insertion into the housing, the removable element having a biopsy needle and a cutting sheath, the cutting sheath configured to couple the electric power source to the tension slide, the electric power source configured to rotate the cutting sheath to move the tension slide to the cocked position; a first control device configured to control the electric power source to rotate the cutting sheath to position the tension slide in the cocked position; and a second control device configured to release the releasable locking mechanism when the tension slide is in the cocked position such that the tension slide is moved by the first spring away from the cocked position.

13. The biopsy device of claim 12, wherein the removable element includes a carrier configured to rotatably mount the cutting sheath, and wherein when the cutting sheath is rotated the cutting sheath is moved both longitudinally and rotationally relative to the carrier.

14. The biopsy device of claim 13, the cutting sheath being rotatable relative to the carrier to effect a longitudinal movement of the cutting sheath relative to the biopsy needle in a proximal direction to open a sample removal chamber of the biopsy needle, and the cutting sheath being rotatable relative to the carrier to effect a longitudinal movement of the cutting sheath along the longitudinal axis relative to the biopsy needle in a distal direction to close the sample removal chamber of the biopsy needle.

15. The biopsy device of claim 12, the removable element including a sample removal chamber and a pump, the pump being coupled in fluid communication with the sample removal chamber.

16. The biopsy device of claim 12, the removable element including a sample removal chamber that is selectively opened and closed by a corresponding longitudinal movement of the cutting sheath, the removable element including a pump to build up pressure at the sample removal when the sample removal chamber is closed.

17. The biopsy device of claim 16, the electric power source configured to move the cutting sheath in a proximal direction across the sample removal chamber to release the pressure from the sample removal chamber.

18. The biopsy device of claim 12, the removable element including a pump having an elongate cylinder and a plunger, the pump being coupled in fluid communication with a portion of the removable element that includes a sample removal chamber, the pump configured such that moving the plunger inside the elongate cylinder in a first direction generates a vacuum at the sample removal chamber and moving the plunger inside the elongate cylinder in a second direction opposite the first direction builds pressure at the sample removal chamber.

19. The biopsy device of claim 12, wherein the removable element has a knob coupled to the biopsy needle, the biopsy needle having a sample removal chamber, wherein a manual rotation of the knob results in a positioning of the sample removal chamber at a selected rotational position.

\* \* \* \* \*

UNITED STATES PATENT AND TRADEMARK OFFICE
CERTIFICATE OF CORRECTION

PATENT NO. : 10,271,827 B2
APPLICATION NO. : 15/240427
DATED : April 30, 2019
INVENTOR(S) : Norbert Heske et al.

Page 1 of 1

It is certified that error appears in the above-identified patent and that said Letters Patent is hereby corrected as shown below:

In the Specification

At Column 1 Lines 6-20:
"This is a continuation of U.S. patent application Ser. No. 14/729,113, filed Jun. 3, 2015, which is a continuation of U.S. patent application Ser. No. 13/340,115, filed Dec. 29, 2011, now U.S. Pat. No. 9,072,502, which is a continuation of U.S. patent application Ser. No. 10/500,522, filed Apr. 6, 2005, now U.S. Pat. No. 8,109,885, which is a national stage application under 35 U.S.C. § 371 of International Application PCT/DE2003/00844, filed Mar. 17, 2003, which claims priority to DE20201363.0, filed Mar. 19, 2002, DE20204362.2,2, filed Mar. 19, 2002, DE20204361.4, filed Mar. 19, 2002, DE102121567.7, filed Mar. 19, 2002, DE10212139.7, filed Mar. 19, 2002, DE10212155.9, filed Mar. 19, 2002, DE20209525.8, filed Jun. 19, 2002, DE20209530.4, filed Jun. 19, 2002, DE20211934.3, filed Aug. 2, 2002, and DE20215962.0, filed Oct. 17, 2002."

Should be:
---This is a continuation of U.S. patent application Ser. No. 14/729,113, filed Jun. 3, 2015, which is a continuation of U.S. patent application Ser. No. 13/340,115, filed Dec. 29, 2011, now U.S. Pat. No. 9,072,502, which is a continuation of U.S. patent application Ser. No. 10/500,522, filed Apr. 6, 2005, now U.S. Pat. No. 8,109,885, which is a national stage application under 35 U.S.C. § 371 of International Application PCT/DE2003/00844, filed Mar. 17, 2003, which claims priority to DE20204363.0, filed Mar. 19, 2002, DE20204362.2, filed Mar. 19, 2002, DE20204361.4, filed Mar. 19, 2002, DE10212156.7, filed Mar. 19, 2002, DE10212139.7, filed Mar. 19, 2002, DE10212155.9, filed Mar. 19, 2002, DE20209525.8, filed Jun. 19, 2002, DE20209530.4, filed Jun. 19, 2002, DE20211934.3, filed Aug. 2, 2002, and DE20215962.0, filed Oct. 17, 2002.---

Signed and Sealed this
Sixth Day of August, 2019

Andrei Iancu
*Director of the United States Patent and Trademark Office*